(12) United States Patent
Wang

(10) Patent No.: US 8,084,641 B2
(45) Date of Patent: Dec. 27, 2011

(54) ORGANOCATASLYSTS AND METHODS OF USE IN CHEMICAL SYNTHESIS

(75) Inventor: Wei Wang, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 1433 days.

(21) Appl. No.: 11/546,092

(22) Filed: Oct. 11, 2006

(65) Prior Publication Data

US 2009/0088588 A1    Apr. 2, 2009

Related U.S. Application Data

(60) Provisional application No. 60/725,754, filed on Oct. 11, 2005.

(51) Int. Cl.
*C07C 335/20* (2006.01)
*C07C 275/40* (2006.01)

(52) U.S. Cl. .......................................... 564/27; 564/50

(58) Field of Classification Search .................... 564/27, 564/50
See application file for complete search history.

(56) References Cited

OTHER PUBLICATIONS

Stibor et al., Collection of Czechoslovak Chemical Communications (2004), 69(2), pp. 365-383.*
P. Perlmutter, Conjugate Addition Reactions in Organic Synthesis, Pergamon, Oxford, 1992.
N. Krause, A. Hoffmann-Röder, Synthesis 2001, 171.
O. M. Berner, L. Tedeschi, D. Enders, Eur. J. Org. Chem. 2002, 1877-1894.
J. Christoffers, A. Baro, Angew. Chem. 2003, 115, 1726.
J. Christoffers, A. Baro, Angew. Chem. Int. Ed, 2003, 42, 1688.
M. Sibi, S. Manyem, Tetrahedron 2001, 56, 8033.
N. Ono, H. Miyake, A. Kamimura, L. Hamamoto, R. Tamura, A. Kaji, Tetrahedron 1985, 41, 4013.
T. A. Johnson, D. O. Jang, B. W. Slafer, M. D. Curtis, P. Beak, J. Am. Chem. Soc. 2002, 11689.
H. Schäfer, D. Seebach, Tetrahedron 1995, 51, 2305.
A. M. Rouhi, C & En. 2004, 82, 41.
N. Kobayashi, K. Iwai, J. Org. Chem. 1981, 46, 1823.
C. A. Luchaco-Cullis, A. H. Hoveyda, J. Am. Chem. Soc. 2002, 124, 8192.
A. Alexakis, C. Benhaim, S. Rosset, M. Humam, J. Am. Chem. Soc. 2002, 124, 5262.
A. Rimkus, N. Sewald, Org. Lett. 2003, 5, 79.
W. Wang, J. Wang, H. Li, Angew. Chem. 2005, 117, 1395.
W. Wang, J. Wang, H. Li, Angew. Chem. Int. Ed. 2005, 43, 1369.
B. List, P. Pojarliev, H. J. Martin, Org. Lett. 2001, 3, 2423.
D. Ender, A. Seki, Synlett 2002, 26.
N. Mase, R. Thayumanavan, F. Tanaka, C. F. Barbas, III, Org. Lett. 2004, 6, 2527.
J. M. Betancort, K. Sakthivel, R. Thayumanavan, F. Tanaka, C. F. Barbas, III, Synthesis 2004, 1509.
O. Andrey, A. Alexakis, G. Bernardinelli, Org. Lett. 2003, 5, 2559.
T. Ishii, S. Fiujioka, Y. Sekiguchi, H. Kotsuki, J. Am. Chem. Soc. 2004, 126, 9558.
A. J. A. Cobb, D. A. Longbottom, D. M. Shaw, S. V. Ley, Chem. Commun. 2004, 1808.
Y. Hayashi, T. Gotoh, T. Hayasji, M. Shoji, Angew. Chem. 2005, 117, 4284; Y.
Hayashi, T. Gotoh, T. Hayasji, M. Shoji, Angew. Chem. Int. Ed. 2005, 44, 4212.
P. Kotrusz, S. Toma, H.-S. Schmalz, A. Adler, Eur. J. Org. Chem. 2005, 1577.
T. Okino, Y. Hoashi, Y. Takemoto, J. Am. Chem. Soc. 2003, 125, 12672.
T. Okino, Y. Hoashi, T. Furukawa, X. Xu, Y. Takemoto, J. Am. Chem. Soc. 2005, 127, 119.
H. Li, Y. Wang, L. Tang, L. Deng, J. Am. Chem. Soc. 2004, 126, 9906.
H. Li, Y. Wang, L. Tang, F. Wu, X. Liu, C. Guo, B. M. Foxman, L. Deng, Angew. Chem. Int. Ed. 2005, 44, 105.
P. M. Pihko, Angew. Chem. Int. Ed. 2004, 43, 2062.
J. Seayad, B. List, Org. Biomol. Chem. 2005, 3, 719.
M. S. Sigman, E. N. Jacobsen, J. Am. Chem. Soc. 1998, 120, 4901.
M. S. Sigman, P. Vachal, E. N. Jacobsen, Angew. Chem. 2000, 112, 1336.
M. S. Sigman, P. Vachal, E. N. Jacobsen, Angew. Chem. Int. Ed. 2000, 39, 1279.
P. Vachal, E. N. Jacobsen, J. Am. Chem. Soc. 2002, 124, 10012.
T. P. Yoon, E. N. Jacobsen, Angew. Chem. 2005, 117, 470.
T. P. Yoon, E. N. Jacobsen, Angew. Chem. Int. Ed. 2005, 44, 466.
G. D. Joly, E. N. Jacobsen, J. Am. Chem. Soc. 2004, 126, 4102.
M. S. Taylor, E. N. Jacobsen, J. Am. Chem. Soc. 2004, 126, 10558.
T. Okino, S. Nakamura, T. Furukawa, Y. Takemoto, Org. Lett. 2004, 6, 625.
Y. Hoashi, T. Okino, Y. Takemoto, Angew. Chem. 2005, 117, 4100.
Y. Hoashi, T. Okino, Y. Takemoto, Angew. Chem. Int. Ed. 2005, 44, 4032.
B. Vakulya, S. Varga, A. Csampai, T. Soos, Org. Lett. 2005, 7, 1967.
T. P. Yoon, E. N. Jacobsen, Science 2003, 299, 1691.
H. M. L. Davies, P. Ren, Tetrahedron Lett. 2001, 42, 3149.
Basavaiah, D.; Rao, A. J.; Satyanarayana, T. Chem. Rev. 2003, 103, 811.
Langer, P. Angew. Chem. Int. Ed. 2000, 39, 3049.
Iwabuchi, Y.; Nakatani, M.; Yokoyama, N.; Hatakeyama, S. J. Am. Chem. Soc. 1999, 121, 10219.
Yang, K.-S.; Lee, W.-D.; Pan, J.-F.; Chen.K. J. Org. Chem. 2003, 68, 915.
McDougal, N. T.; Schaus, S. E. J. Am. Chem. Soc. 2003, 125, 12094.
Shi, M.; Jiang, J.-K.; Li, C.-Q. Tetrahedron Lett. 2001, 42, 127.
Imbriglio, J. E.; Vasbinder, M. M.; Miller, S. J. Org. Lett. 2003, 5, 3741.

(Continued)

*Primary Examiner* — Peter O Sullivan
(74) *Attorney, Agent, or Firm* — Henry D. Coleman; R. Neil Sudol; William J. Sapone

(57) ABSTRACT

The present invention is directed to compositions comprising organocatalysts that facilitate stereo-selective reactions and the method of their synthesis and use. Particularly, the invention relates to metal-free organocatalysts for facilitation of stereo-selective reactions, and the method of their synthesis and use.

19 Claims, 3 Drawing Sheets

OTHER PUBLICATIONS

Oishi, T.; Oguri, H.; Hirama, M. Tetrahedron: Asymmetry 1995, 6, 1241.
Marko, I. E.; Giles, P. R.; Hindley, N. J. Tetrahedron 1997, 53, 1015.
Barrett, A. G. M.; Cook, A. S.; Kamimura, A. Chem. Commun. 1998, 2533.
Sohtome, Y.; Tanatani, A.; Hashimoto, Y.; Nagasawa, K. Tetrahedron Lett. 2004, 45, 5589.
Karur, S.; Hardin, J.; Headley, A.; Li, G. Tetrahedron Lett. 2003, 44, 2991.
Pei, W.; Wei, H.-X.; Li, G. Chem. Commun. 2002, 2412.
Pei, W.; Wei, H.-X.; Li, G. Chem. Commun. 2002, 1856.
Shi, M.; Chen, L.-H.; Li, C.-Q. J. Am. Chem. Soc. 2005, 127, 3790.
Shi, Y. Acc. Chem. Res. 2004, 37, 4886.
Shi, M.; Xu, Y.-M. Angew. Chem. Int. Ed. 2002, 41, 4507.
Perlmutter, P.; Teo, C. C. Tetrahedron Lett. 1984, 25, 5951.
Balan, D.; Adolfsson, H. J. Org. Chem. 2001, 66, 6498.
Bertenshaw, S.; Kahn, M. Tetrahedron Lett. 1989, 30, 2731.
Aggarwal, V. K.; Mereu, A.; Tarver, G. J.; McCague, R. J. Org. Chem. 1998, 63, 7183.
Azizi, N.; Saidi, M. R. Tetrahedron Lett. 2002, 43, 4305.
Richter, H.; Jung, G. Tetrahedron Lett. 1998, 39, 2729.
Takagi, M.; Yamamoto, K. Tetrahedron 1991, 47, 8869.
Matsui, K.; Takizawa, S.; Sasai, H. J. Am. Chem. Soc. 2005, 127, 3680.
Shibasaki, M.; Sasai, H.; Arai, T. Angew. Chem. Int. Ed. 1997, 36, 1236.
Wang, W.; Wang, J.; Li, H. Angew. Chem. Int. Ed. 2005, 43, 1369.
Breinbauer, R.; Jacobsen, E. N. Angew. Chem. Int. Ed. 2000, 39, 3604.
Seayad, J.; List, B. Org. Biomol. Chem. 2005, 3, 719.
Pihko, P. M. Angew. Chem. Int. Ed. 2004, 43, 2062.
Sigman, M. S.; Jacobsen, E. N. J. Am. Chem. Soc. 1998, 120, 4901.
Sigman, M. S.; Vachal, P.; Jacobsen, E. N. Angew. Chem. Int. Ed. 2000, 39, 1279.
Vachal, P.; Jacobsen, E. N. J. Am. Chem. Soc. 2002, 124, 10012.
Wenzel, A. G.; Jacobsen, E. N. J. Am. Chem. Soc. 2002, 124, 12964.
Yoon, T. P.; Jacobsen, E. N. Angew. Chem. Int. Ed. 2005, 44, 466.
Joly, G. D.; Jacobsen, E. N. J. Am. Chem. Soc. 2004, 126, 4102.
Taylor, M. S.; Jacobsen, E. N. J. Am. Chem. Soc. 2004, 126, 10558.
Okino, T.; Hoashi, Y.; Takemoto, Y. J. Am. Chem. Soc. 2003, 125, 12672.
Okino, T.; Hoashi, Y.; Furukawa, T.; Xu, X.; Takemoto, Y. J. Am. Chem. Soc. 2005, 127, 119.
Okino, T.; Nakamura, S.; Furukawa, T.; Takemoto, Y. Org. Lett. 2004, 6, 625.
Hoashi, Y.; Okino, T.; Takemoto, Y. Angew. Chem. Int. Ed. 2005, 44, 4032.
Vakulya, B.; Varga, S.; Csampai, A.; Soos, T. Org. Lett. 2005, 7, 1967.
Yoon, T. P.; Jacobsen, E. N. Science 2003, 299, 1691.
Etter, M. C. Acc. Chem. Res. 1990, 23, 120.
Etter, M. C.; Panunto, T. W. J. Am. Chem. Soc. 1988, 110, 5896.
Etter, M. C.; Urbanczyk-Lipkowska, Z.; Zia-Ebrahimi, M.; Panunto, T. W. J. Am. Chem. Soc. 1990, 112, 8415.

\* cited by examiner

ORGANOCATASLYSTS AND METHODS OF USE IN CHEMICAL SYNTHESIS

RELATED APPLICATIONS

This application claims the benefit of priority of U.S. provisional application No. 60/725,754, filed Oct. 11, 2005, which disclosure is incorporated by reference in its entirety herein.

FIELD OF THE INVENTION

The present invention pertains generally to compositions comprising organocatalysts that facilitate stereo-selective reactions and the method of their synthesis and use. Particularly, the invention relates to metal-free organocatalysts for facilitation of stereo-selective reactions, and the method of their synthesis and use.

BACKGROUND OF THE INVENTION

The growing demand for chiral non-racemic compounds and drugs in the pharmaceutical industry has created a formidable synthetic challenge for chemists to find cost-effective and highly stereoselective means to assemble these molecules. Of the various methods available for the preparation of enantiomerically pure compounds, asymmetric catalytic processes are the most attractive. Over the past several decades, the main body of research in catalysis has been focused on transition metal-based organometallic catalysts and significant progress has been made. Surprisingly, however, relatively few asymmetric transformations have been reported which employ organic molecules as reaction catalysts (organocatalysts) despite their enormous potential in asymmetric transformations and widespread availability in optically pure forms.

A chiral molecule is one that is not superimposable on its mirror image. Often referred to as 'handedness," (in fact the term "chirality" derives from the Greek word for "hand") since the property can be demonstrated by examining one's hands, which are mirror images of each other, but which are not superimposable one on the other. A chiral molecule is also observable for having the property of rotating the plane of polarization of plane-polarized monochromatic light passed through it—a phenomenon called "optical activity." Pure solutions of a single stereoisomer (the chiral molecule and its mirror image are called "stereoisomers" or "enantiomers") will rotate the plane of plane polarized light in one direction, and the other enantiomer will rotate polarized light the same number of degrees, but in the opposite direction. For this reason, stereoisomers are often called "optical isomers." A solution that contains an equal mixture of the two optical isomers (a "racemic" mixture) will not change the plane of plane polarized light, because the effects of the two isomers cancel each other out. Pairs of stereoisomers are sometimes indistinguishable one from another in chemical reactions, but can be distinguished by examining a physical property (usually optical) of the molecule.

It has long been known, particularly in the pharmaceutical industry, that often one enantiomer is more effective in a reaction (or in a therapeutic treatment) than its mirror-image counterpart. In fact, in one well documented case of the importance of chirality, the use of a racemic mixture of thalidomide in pregnant women caused severe birth defects in their children. It was determined that one enantiomer was a powerful sedative while the other was toxic. As a result, obtaining a substantially pure form of a single enantiomer is often very desirable.

Given the Laws of Thermodynamics, this proves initially difficult. The left- and right-handed forms have identical free energy (G), so the free energy difference ($\Delta G$) is zero. The equilibrium constant for any reaction (K) is the equilibrium ratio of the concentration of products to reactants. The relationship between these quantities at any Kelvin temperature (T) is given by the standard equation:

$$K = \exp(-\Delta G/RT)$$

wherein R is the universal gas constant (Avogadro's number×Boltzmann's constant k)=8.314 J/K·mol. For the reaction of changing left-handed to right-handed amino acids (L→R), or the reverse (R→L), $\Delta G$=0, so K=1. That is, the reaction reaches equilibrium when the concentrations of R and L are equal; that is, a racemate is produced.

For separation of or "resolving" a racemate (i.e., separate the two enantiomers), another homochiral substance is usually introduced. The idea is that right-handed and left-handed substances have identical properties, except when interacting with other chiral phenomena. The analogy is that our left and right hands grip an achiral (non-chiral) object like a stick equally, but they fit differently into a chiral object like a left-handed glove. Thus to resolve a racemate, an organic chemist will usually use a ready-made homochiral substance from a living organism. The reaction products of the R and L enantiomers with an exclusively right-handed substance R', that is R-R' and L-R' (called diastereomers), are not mirror images. So they have different physical properties, e.g. solubility in water, and thus they can be separated.

This often requires a homo-chiral substance to separate the enantiomers and the ability to separate the substance from the desired enantiomer. While available for separation of some chiral substances, such substances are certainly not readily available for all. Chemists have tried other ways to reach their goal of substantially pure enantiomers, including asymmetric synthesis, wherein only one enantiomer is produced in synthesis of the compound, thereby eliminating the need to resolve a racemate.

In particular, asymmetric synthesis of optically active natural and unnatural α-amino acids has been of long-standing interest to organic chemists since these substances are versatile synthetic building blocks for the preparation of an assortment of biologically important molecules. In this regard, the enantioselective Mannich-type reaction of an enolate or enolate equivalent with α-imino ester constitutes a powerful approach to the synthesis of novel functionalized γ-keto-α-amino acid derivatives. S. E. Denmark, O. J.-C. Nicaise In *Comprehensive Asymmetric Catalysis*, (Eds.; E. N. Jacobsen, A. Pfaltz, H. Yamamoto), Springer, Heidelberg, 1999, pp 926; b) D. Arend, B. Westermann, N. Risch, *Angew. Chem.* 1998, 110, 1096-1122; D. Arend, B. Westermann, N. Risch, *Angew. Chem. Int. Ed.* 1998, 37, 1044-1070.

Over the past few years, catalytic, enantioselective versions of this process have received great attention with emphasis being given to the development of organometallic catalysis. S. E. Denmark, O. J.-C. Nicaise In *Comprehensive Asymmetric Catalysis*, (Eds.; E. N. Jacobsen, A. Pfaltz, H. Yamamoto), Springer, Heidelberg, 1999, pp 926; b) D. Arend, B. Westermann, N. Risch, *Angew. Chem.* 1998, 110, 1096-1122; D. Arend, B. Westermann, N. Risch, *Angew. Chem. Int. Ed.* 1998, 37, 1044-1070; H. Ishitani, M. Ueno, S. Kobayashi, *J. Am. Chem. Soc.* 1997, 119, 7153-7154; b) S. Kobayashi, T. Hamada, K. Manabe, *J. Am. Chem. Soc.* 2002, 124, 5640-5641; c) H. Ishitani, S. Ueno, S. Kobayashi, *J. Am. Chem. Soc.*

2000, 122, 8180-8186; E. Hagiwara, A. Fujii, M. Sodeoka, *J. Am. Chem. Soc.* 1998, 120, 2474-2475; b) A. Fujii, E. Hagiwara, M. Sodeoka, *J. Am. Chem. Soc.* 1999, 121, 545-556; D. Ferraris, B. Young, T. Dudding, T. Lectka, *J. Am. Chem. Soc.* 1998, 120, 2474-2475; b) D. Ferraris, B. Young, C. Cox, T. Dudding, W. J. Drury, III, L. Ryzhkov, T. Taggi, T. Lectka, *J. Am. Chem. Soc.* 2002, 124, 67-77.

However, these metal-based catalysis methods rely on the use of pre-formed enolates or enolate equivalents. An effective, atom-economic asymmetric version of this reaction, employing unmodified carbonyl compounds would be more attractive from a synthesis standpoint. The examples of such reactions catalyzed by organometallic-based chiral catalysts have been described by Shibasaki, Trost and Jørgensen. S. Yamasaki, T. Iida, M. Shibasaki, *Tetrahedron Lett.* 1999, 40, 307-310; B. M. Trost, L. M. Terrell, *J. Am. Chem. Soc.* 2003, 125, 338-339; K. Juhl, N. Gathergood, K. A. Jørgensen, *Angew. Chem.* 2001, 113, 3083-3085; K. Juhl, N. Gathergood, K. A. Jørgensen, *Angew. Chem. Int. Ed.* 2001, 40, 2995-2997.

The development of metal-free organo-catalysts has emerged as a new frontier in asymmetric catalysis, pioneered by List, Barbas III, and MacMillan. P. I. Dalko, L. Moisan, *Angew. Chem.* 2001, 113, 3840-3864; P. I. Dalko, L. Moisan, *Angew. Chem. Int. Ed.* 2001, 40, 3726-3748; b) a review of proline catalyzed reactions: B. List, *Tetrahedron* 2002, 58, 5573-5590; B. List, R. A. Lerner, C. F. Barbas III, *J. Am. Chem. Soc.* 2000, 122, 2395-2396; K. A. Ahrendt, C. J. Borths, D. W. C. MacMillan, *J. Am. Chem. Soc.* 2000, 122, 4243-4244.

Several catalytic systems including L-proline, peptides and small organic molecules have been reported for the Mannich reactions. B. List *J. Am. Chem. Soc.* 2000, 122, 9336-9337; B. List, P. Pojarliev, W. T. Biller, H. J. Martin, *J. Am. Chem. Soc.* 2002, 124, 827-833; Y. Hayashi, W. Tsuboi, M. Shoji, N. Suzuki, *J. Am. Chem. Soc.* 2003, 125, 11208-11209; Y. Hayashi, W. Tsuboi, I. Ashimine, T. Urushima, M. Shoji, K. Sakai, *Angew. Chem.* 2003, 115, 3805-3808; Y. Hayashi, W. Tsuboi, I. Ashimine, T. Urushima, M. Shoji, K. Sakai, *Angew. Chem. Ed. Engl.* 2003, 42, 3677-3680; A. Córdova, W. Notz, G. Zhong, J. M. Betancort, C. F. Barbas III, *J. Am. Chem. Soc.* 2002, 124, 1842-1843; b) A. Córdova, S. Watanabe, F. Tanaka, W. Notz, C. F., Barbas III, *J. Am. Chem. Soc.* 2002, 124, 1866-1867; c) A. Córdova, C. F. Barbas III, *Tetrahedron Lett.* 2003, 44, 1923-1926; P. Vachal, E. N. Jacobsen, *J. Am. Chem. Soc.* 2002, 124, 10012-10013; b) A. G. Wenzel, E. N. Jacobsen, *J. Am. Chem. Soc.* 2002, 124, 12964-12965. Only the L-proline catalyzed process described by Barbas III (referenced above) and his co-workers promotes direct Mannich-type reactions of ketones and aldehydes with α-imino esters.

Compared with traditional metal-ligand complex catalysts, it is surprisingly found that metal-free organo-catalysts are less expensive, benign to the environment, easy to prepare and handle, and are air-stable, and non-sensitive to moisture. Therefore, the field would be greatly enhanced with the development of novel metal-free organo-catalysts which reduce time, effort, and amount of reactant necessary to arrive at a single enantiomer product. In turn, industries such as the pharmaceutical industry which require such purified forms can reduce the cost of and improve the quality of their ultimate product.

One of the important Michael addition reactions is the addition of nucleophiles to electron deficient nitroalkenes.[1,2] Because the versatile nitro functionality can be easily transformed into amine, nitrile oxide, ketone or carboxylic acid, hydrogen, etc.,[2b] various enantioselective processes have been reported mainly by employing stoichiometric amounts of enantiopure additives.[3] And also the catalytic asymmetric versions of this reaction were achieved by using chiral metal-ligand complexes.[4] Recently, we and others have developed more environmental friendly metal-free organocatalysts to catalyze efficient asymmetric Michael addition reactions.[5-7] In these approaches, the donors employed in these processes have been restricted to aldehydes and ketones,[5] malonate esters,[6] and ketoesters.[7] Herein, we wish to report a novel type of organocatalysts, bifunctional binaphthyl-derived amine thioureas, which have been first demonstrated for catalyzing highly enantioselective Michael addition reactions using 1,3-diketones as donors. Furthermore, in the preliminary study, we have demonstrated that the Michael adducts can be readily converted to synthetically and biologically useful building blocks α-substituted-β-amino acids.

In the past few years, the utilization of chiral ureas/thioureas has emerged as a viable strategy in the design of efficient organocatalysts for asymmetric organic transformations.[6, 8-11] Notable examples include Jacobsen's ureas/thioureas for catalyzing a variety of reactions[9] and Takemoto's amine thioureas for Michael addition and aza-Henry reactions.[6a,b, 10] It is noted that both catalyst systems are built upon the trans-cyclohexane diamine scaffold. More recently, cinchona alkaloids-based thioureas have been employed for Michael addition reaction as well.[11] However, thioureas derived from another important "privileged" structure binaphthyl have not been reported yet.[12] We envisioned that the inclusion of a thiourea and an amine moiety into the scaffold could lead to a new class of bifunctional organocatalysts, which would provide high catalytic activity and enantioselectivity toward organic reactions. The results from this investigation disclosed that a newly designed organocatalyst VII (see below) displayed remarkably catalytic activity (1 mol % catalyst loading) on the processes with achieving excellent levels of enantioselectivities (up to 97% ee).

Separately, in recent years, the Morita-Baylis-Hillman (MBH) reaction, which involves forming new C—C bonds and generating highly functionalized chiral allylic alcohols, has received considerable interest in organic synthesis.[1a] Therefore, not surprisingly, a considerable amount of effort has been devoted to the development of catalytic, enantioselective versions of the processes. However, discovering catalytic systems for asymmetric MBH reactions has proven to be a synthetic challenge, and to date, a very limited number of successful chiral catalysts have been demonstrated for this process.[2a,3a] Among them, notably, the research groups of Hatakeyama[2aa] and Chen[2ab] respectively, have developed quinidine-based chiral amines and chiral Lewis acids as catalysts for promoting addition of acrylates to aldehydes. Schaus et al[2ac] reported an elegant BINOL derived Brønsted acid, and Shi[2ad] and Miller[2ae] independently used an amino acid L-proline as organocatalyst for the asymmetric MBH reactions of α, β-unsaturated ketones with aldehydes. However, both cases require adding a Lewis base for facilitating the reactions. From an operational and atom-economic standpoint, the utilization of bifunctional catalysts is highly desirable, but such catalysts have not been developed yet. Moreover, generally, a bifunctional catalyst can activate two functional groups in their substrates via synergistic interactions and, thus, specifically control transition state structure, leading to higher catalytic activity and better enantioselectivity.[4a] In this communication, we wish to first report a novel type of bifunctional organocatalyst, the chiral amine-thiourea for catalyzing highly enantioselective MBH reactions.

BRIEF DESCRIPTION OF THE INVENTION

Figure 1:
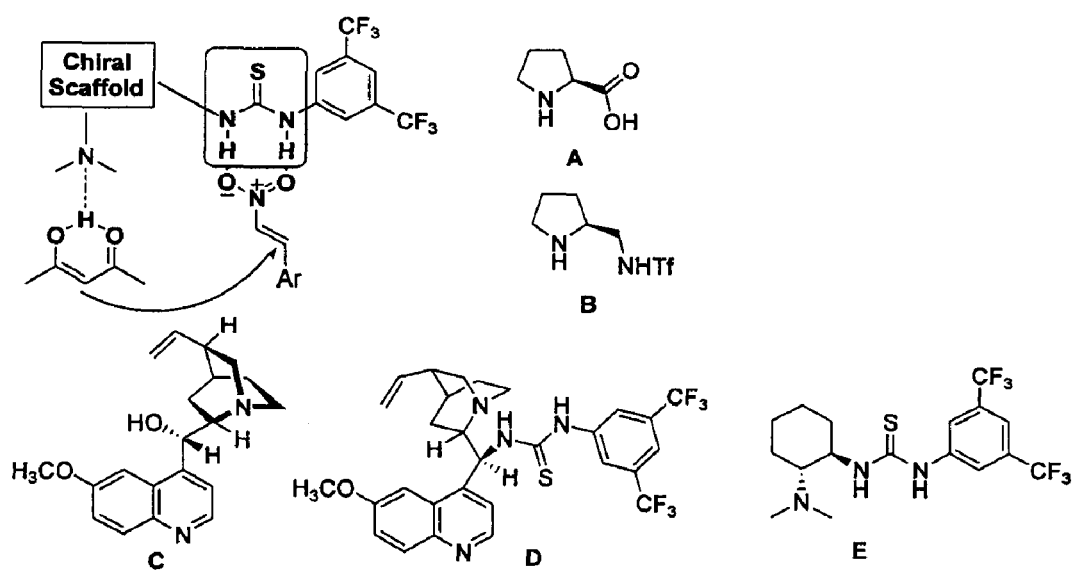
FIG. 1 shows a number of screened catalysts.

The present invention is directed to compounds according to the general structures I-VIII below:

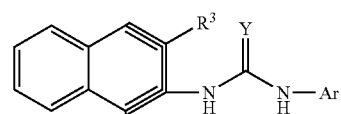

I

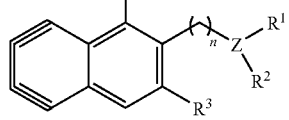

II

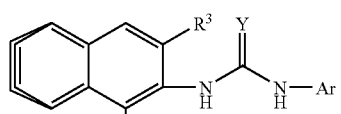

III

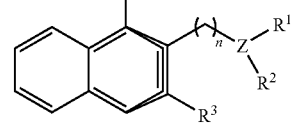

IV

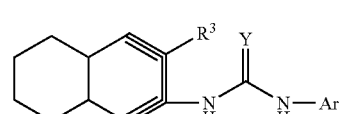

V

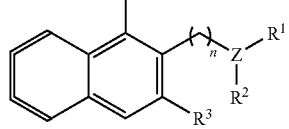

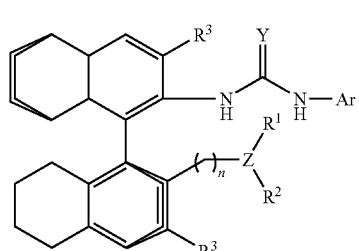

VI

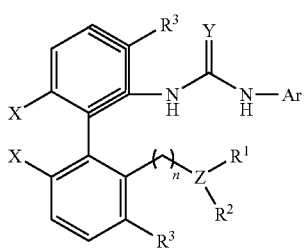

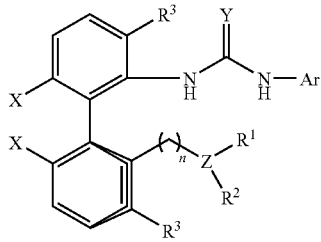

VII

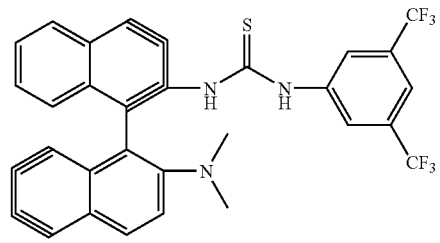

Where Y is O or S;
Z is N or P;
n is 0-6;
$R^1$ and $R^2$ are independently H, an optionally substituted $C_1$-$C_{10}$ hydrocarbyl group, preferably an alkyl group (preferably, $C_1$-$C_8$ alkyl) or a three- to seven-membered optionally substituted heterocyclic group or together with the nitrogen to which they are attached, $R^1$ and $R^2$ form a five or six membered heterocyclic ring;
$R^3$ is H, halogen (F, Cl, Br, I, preferably F), CN, $NO_2$, a $CO_2R$ group, wherein R is an optionally substituted aromatic (preferably phenyl), including a heteroaromatic group, or an optionally substituted $C_1$-$C_6$ alkyl group (preferably substituted with F);
Ar is an optionally substituted aromatic group (preferably, phenyl), including an optionally substituted heteroaromatic group;
X is an optionally substituted aromatic, including an optionally substituted heteroaromatic group, $OR^4$ or $N(R^4)_2$, where each $R^4$ is independently an optionally substituted $C_1$-$C_6$ alkyl group, an optionally substituted $C_3$-$C_7$ carbocyclic group, an optionally substituted aromatic group or a 3- to 7-membered heterocyclic group, or a salt thereof.

The present compounds are useful for catalyzing numerous stereoselective reactions to produce useful intermediates or final compounds, especially pharmaceutically active compounds, including amino acids and related compounds.

Methods of using the above-described organic catalysts to produce chiral allylic alcohols represent another aspect of the invention. Still another aspect of the invention is to catalyze Michael Addition reactions of aldehydes or ketones to nitroolefins including nitrostyrenes to produce Michael adducts which may be converted to amino acids, especially α-substituted-β-amino acids.

Catalytic compounds according to the invention may be used to catalyze the above reactions, in many instances with high stereo- and/or enantiomeric selectivity in good to excellent yield:

In general in the above methods, the organocatalyst is used in an amount ranging from about 0.01% to about 30 mol % (based upon the amount in moles of the reactant included in greatest amount), preferably about 0.5 mol % to about 25 mol %, preferably about 1% to about 20 mol %, also about 2 mol % to about 20 mol %. These methods are presented in greater detail in the sections which follow.

DETAILED DESCRIPTION OF THE INVENTION

As used herein, the following terms are used to describe the present invention. The definitions provided below, within context, may be used exclusively, or may be used to supplement definitions which are generally known to those of ordinary skill in the art.

Unless otherwise indicated, the present invention is not limited to particular molecular structures, substituents, synthetic methods, reaction conditions, or the like, and accordingly, these may vary. It is also to be understood that the terminology used herein is for the purpose of describing particular embodiments only and is not intended to be limiting.

As used in the specification and the attached claims, the use of "a," "an" and "the" include references to plural subject matter referred to unless the context clearly dictates otherwise. Thus, for example, reference to "a catalyst" includes a single catalyst as well as a combination or mixture of two or more catalysts, reference to "a reactant" encompasses a combination or mixture of different reactants as well as a single reactant, and the like.

A term which is subsumed under another term may be embraced by the broader term or by the more narrow specific term as appropriate within the context of the use of that term. All terms used to describe the present invention are used within context.

In this specification and in the claims that follow, reference will be made to a number of terms, which shall be defined to have the following meanings:

As used herein, the phrase "according to the formula", "having the formula" or "having the structure" is not intended to be limiting and is used in the same way that the term "comprising" is commonly used. The term "independently" is used herein to indicate that the recited elements, e.g., R groups or the like, can be identical or different.

"Optional" or "optionally" means that the subsequently described circumstance may or may not occur, so that the description includes instances where the circumstance occurs and instances where it does not. For example, the term "optionally substituted" means that a non-hydrogen substituent may or may not be present on a given atom, and, thus, the description includes structures where a non-hydrogen substituent is present and structures where a non-hydrogen substituent is not present.

The term "compound", as used herein, unless otherwise indicated, refers to any specific chemical compound disclosed herein and includes in context, tautomers, regioisomers (especially cis/trans), geometric isomers, and where applicable, optical isomers thereof, as well as appropriate salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. The compounds of this invention include all stereoisomers where relevant (e.g., cis and trans isomers) and all optical isomers of the present compounds (e.g., R and S enantiomers), as well as racemic, diastereomeric and/or other mixtures of such isomers, as well as all relevant salt forms, solvates and polymorphs of the present compounds, where applicable. As used herein a bold line signifies (especially as it relates to organocatalysts according to the present invention) that a bond disposes that portion of the molecule in a direction away or "out from" the plane of the paper. Other portions of the molecule which are not in bold are disposed in a direction in toward the plane of the paper. In this way, aromatic groups in the organocatalysts according to the present invention are found in an orientation perpendicular to each other within the organocatalyst molecule.

The term "effective" is used in context to describe an amount of a compound, component, condition or other aspect of the invention which occurs in an amount or at a level which is sufficient to effect an intended result, whether that compound, component or condition is an organocatalyst according to the present invention, a solvent, a reactant, an amount of heat or other aspect of the invention.

The term "independently" is used herein to indicate that the variable, which is independently applied, varies independently from application to application.

The term "non-existent" or "absent" refers to the fact that a substituent is absent and the group to which such substituent is attached forms an additional bond with an adjacent atom or group.

The term "optionally substituted" means optional substitution with the specified groups, radicals or moieties. It should be noted that any atom with unsatisfied valences in the text, schemes, examples and tables herein is assumed to have the hydrogen atom(s) to satisfy the valences.

"Alkyl" refers to a fully saturated monovalent hydrocarbyl radical containing carbon and hydrogen, and which may be cyclic, branched or a straight chain. Examples of alkyl groups are methyl, ethyl, n-butyl, n-hexyl, n-heptyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_7$ alkyl groups, cyclic groups are preferably $C_3$-$C_7$ cyclic groups. Alkene refers to a hydrocarbyl radical (radical containing carbon and hydrogen) which has one unsaturated bond. As used herein in context hydrocarbyl radicals (which may be optionally substituted) may be fully saturated (alkyl), contain at least one double bond (alkene), contain at least one a triple bond (alkyne) or may be fully unsaturated (e.g., aromatic)

The term "aryl" or "aromatic" refers to a substituted or unsubstituted monovalent aromatic radical having a single ring (e.g., benzene or phenyl) or multiple condensed rings (e.g., naphthyl, anthracenyl, phenanthryl) and can be can be bound to compound according to the present invention at any position on the ring(s). Other examples of aryl groups include heterocyclic aromatic ring systems "heteroaryl" having one or more nitrogen, oxygen, or sulfur atoms in the ring, such as imidazole, furyl, pyrrole, pyridyl, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole and other non-fused or fused ring systems, among others, which may be substituted or unsubstituted.

The term "heterocycle" or "heterocyclic" shall mean an optionally substituted moiety which is cyclic and contains at least one atom other than a carbon atom, such as a nitrogen, sulfur, oxygen or other atom and is a three- to seven-membered ring. A heterocyclic ring shall contain up to four atoms other than carbon selected from nitrogen, sulfur and oxygen. These rings may be saturated or have unsaturated bonds. Fused rings are also contemplated by the present invention. A heterocycle according to the present invention is an optionally substituted imidazole, a piperazine (including piperazinone), piperidine, furan, pyrrole, imidazole, thiazole, oxazole or isoxazole group, among numerous others. Depending upon its use in context, a heterocyclic ring may be saturated and/or unsaturated. In instances where a heterocyclic ring is fully unsaturated, there is overlap with the term "heteroaryl", as described above.

The term "unsubstituted" shall mean substituted only with hydrogen atoms. The term "substituted" shall mean, within the chemical context of the catalyst compound defined, a substituent (each of which substituents may itself be substituted) selected from a hydrocarbyl (which may be substituted itself, preferably with an optionally substituted alkyl or halogen (one or more fluoro) group(s), among others), preferably a $C_1$-$C_6$ optionally substituted alkyl, an optionally substituted aryl (which also may be heteroaryl and may include an alkylenearyl or alkyleneheteroaryl), an optionally substituted heterocycle (especially including an alkyleneheterocycle), formyl, $C_2$-$C_4$ acyl, $CF_3$, $CF_2CF_3$, halogen (especially fluoro or chloro), CN or nitro. Various optionally substituted moieties may be substituted with 5 or more substituents, preferably no more than 3 substituents and preferably from 1 to 3 substituents. Preferably, substituents most useful in the organic catalyst aspect of the present invention (as opposed to the method of using the catalysts to produce intermediates or final compounds using those catalysts) include the electron withdrawing substituents such as F, Cl, Br, I, $CF_3$, $CF_2CF_3$, CN, $NO_2$, etc, although other groups such as $C_1$-$C_6$ alkyl groups or O—($C_1$-$C_6$) alkoxy groups preferably may be used (where an electron neutral or contributing is desired). Preferred electron withdrawing groups include, in particular, fluorinated alkyl groups, especially $CF_3$ and $CF_2CF_3$, fluoro or chloro groups, CN, or $NO_2$.

Alternatively, substituents on intermediates and reactants in the synthetic methods according to the present invention which are used within the context of the synthetic chemical techniques utilized (any one or more of these substituents may also be used in the catalytic aspects of the invention in context) include, for example, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—(CO)—Z where Z is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡C—), cyanato (—O—C≡N), isocyanato (—O—$N^+$≡$C^-$), isothiocyanato (—S—C≡N), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2O$—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl —(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl (preferably, $C_1$-$C_{20}$ alkyl, more preferably $C_1$-$C_{12}$ alkyl, most preferably $C_1$-$C_6$ alkyl), $C_2$-$C_{24}$ alkenyl (preferably $C_2$-$C_{20}$ alkenyl, more preferably $C_2$-$C_{12}$ alkenyl, most preferably $C_2$-$C_6$ alkenyl), $C_2$-$C_{24}$ alkynyl (preferably $C_2$-$C_{20}$ alkynyl, more preferably $C_2$-$C_{12}$ alkynyl, most preferably $C_2$-$C_6$ alkynyl), $C_5$-$C_{30}$ aryl (preferably $C_5$-$C_{20}$ aryl, more preferably $C_5$-$C_{12}$ aryl), and $C_6$-$C_{30}$ aralkyl (preferably $C_6$-$C_{20}$ aralkyl, more preferably $C_6$-$C_{12}$ aralkyl). In addition, the aforementioned functional groups may, if a particular group permits within the context of a reaction pathway or synthesis, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated. Substitutions which are cyclic groups may be bonded to a single atom within a moiety or more than one substituent may be joined to form a cyclic ring, thus forming for example, bi- or tricyclic groups. Where hydrocarbyl substituents are described as above, preferably, the number of carbons in a substituent ranges from a low of one carbon ($C_1$) or two carbons ($C_2$) to a high of about 4 carbons ($C_4$), 5 carbons ($C_5$), 6 carbons ($C_6$), 7 carbons ($C_7$), 8 carbons ($C_8$), 9 carbons ($C_9$), 10 carbons ($C_{10}$), 15 carbons ($C_{15}$) or 20 or more carbons ($C_{20}$).

When the term "substituted" appears prior to a list of possible substituted groups, it is intended that the term apply to every member of that group. For example, the phrase "substituted alkyl and aryl" or "substituted alkyl or aryl" is to be interpreted as "substituted alkyl and substituted aryl" or "substituted alkyl or substituted aryl."

The term "chiral" refers to a structure that does not have an improper rotation axis ($S_n$), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt. % (95% ee) of the composition in which it is contained, more preferably at least about 99 wt. % (99% ee) of that composition, more preferably about 99+wt. % (99+% ee) of that composition.

The term "enantioselective" refers to a chemical reaction that preferentially results in one enantiomer relative to a second enantiomer, i.e., gives rise to a product of which a desired enantiomer represents at least about 50 wt. % of a mixture of chiral products. Preferably, in the enantioselective reactions herein, the desired enantiomer represents at least about 25% enantiomeric enrichment or "ee" of the product, at least about 35% ee, at least about 40% ee, at least about 45% ee, at least about 50% ee, at least about 55% ee, at least about 60% ee, at least about 65% enantiomeric enrichment of the product, preferably at least about 75% ee, at least about 85% ee, at least about 95% ee, at least about 97% ee, at least about 99% ee and at least 99+% ee of the final product.

The term "temperature" is generally used to describe the temperature at which a reaction takes place. In general, reactions according to the present invention may take place at a temperature ranging from significantly below room temperature (e.g., −78° C.) or above temperature (for example, at reflux temperatures which, depending on the boiling point of the solvent used, can be several hundred degrees celcius), but preferably reactions proceed at or about ambient or room temperature (i.e., the temperature of the surrounding laboratory or manufacturing facility).

The term "solvent" is used to describe a medium (typically, but not necessarily inert) in which a reaction takes place using the organocatalysts according to the present invention. Solvents may include polar and non-polar solvents, including, for example, H$_2$O, pyridine, triethanolamine, tetrahydrofuran, 1,4-dioxane, acetonitrile, dimethylacetamide (DMA), dimethylformamide (DMF), dimethylsulfoxide (DMSO), acetonitrile, methylene chloride, nitromethane, chloroform, methanol, ethanol, isopropanol, etc., aqueous alcohol (methanol, ethanol, isopropanol, N-methylpyrrolidone (NMP), ethylacetate, benzene, toluene, diethylether, etc. and mixtures, thereof.

The term "acid" is used (within the context of its use) as it is typically understood by those of ordinary skill in the art to describe a protic acid (proton donor) or Lewis acid for use in the present invention and may include strong acids, such as hydrochloric acid, sulfuric acid, phosphoric acid, sulfamic acid, etc., organic acids, such as acetic acid, benzoic acid, mandelic acid, propionic acid and butyric acid, etc. and a number of Lewis acids well-known in the art, such as AlX$_3$, BX$_3$, FeX$_3$, GaX$_3$, SbX$_3$, SnX4, ZnX$_3$, where X is a halogen atom or an inorganic radical, among numerous others.

The term "base" is used (within the context of its use) as it is typically understood by those of ordinary skill in the art to describe a proton acceptor or Lewis base. Typical bases include sodium or potassium hydroxide, various carbonates, various amines and related typical bases such as pyridine, triethylamine, etc. Lewis bases are electron acceptors which are well-known in the art and include such bases as NH$_3$, PF$_3$, PCl$_3$, H$_2$S, H$_2$O, HOCH$_2$CH$_2$CH$_2$OH, Cl$^-$, OH$^-$, O$_2$CCO$_2^{2-}$, and any negatively charged ion.

The term "protecting group" or "protected" in context, refers to a chemical moiety or group which protects or prevents an active moiety or group from participating with or interfering with one or more chemical synthetic steps and its removal restores the moiety to its original active state. The term protecting group as used herein refers to those groups intended to protect against undesirable reactions during synthetic procedures. Such protecting groups are well known to those skilled in the art and are exemplified in U.S. Pat. No. 5,288,709, as well a large number of other references. Protecting groups can be removed with inter alia acid, base, fluoride ions, hydrogenation, metals such as zinc as well as by numerous other methods which are well known in the art. One of ordinary skill in the art can readily choose an appropriate protecting group to facilitate synthetic reactions according to method aspects of the present invention without engaging in undue experimentation. t-butyl carbamate (BOC), 9-fluorenylmethyl carbamate (FMOC), benzyl carbamate (CBz) and ortho-nitrobenzyl carbamate groups may be used in the present invention. P-methoxyanisidine group (PMP) group is a preferred group for the protection of a nitrogen. The benzyl carbamate (CBz) group is preferred for the protection of hydroxyl groups. Numerous addition groups including acyl groups, benzyl groups, silyl groups, etc. may be used as acceptable protecting groups for synthetic purposes according to the present invention.

The term "isolation" or "isolating" refers to the process or method by which a product compound or composition is isolated from a reaction mixture. These methods may include various forms of chromatography, including those which employ chiral packing or support in columns, including standard column chromatography, medium and high pressure liquid chromatography, crystallization, precipitation, etc., countercurrent distribution, etc. All methods for isolating compounds according to the present invention are well know in the art.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

The present invention preferably relates to chiral catalytic compounds according to the general structure(s):

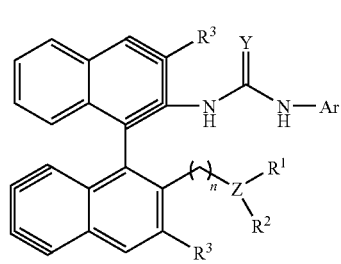

I

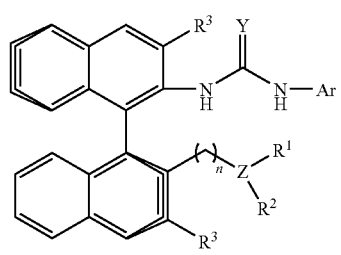

II

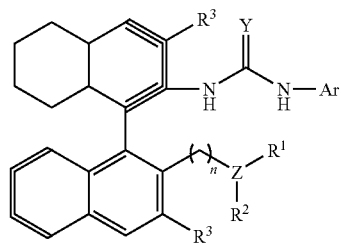

III

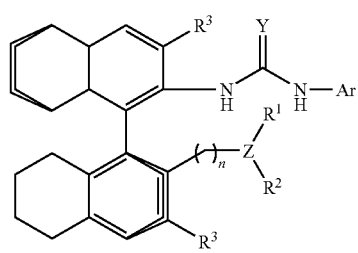

IV

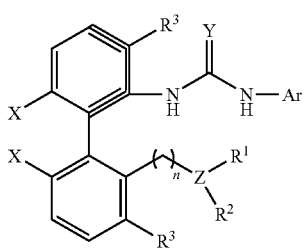

V

-continued

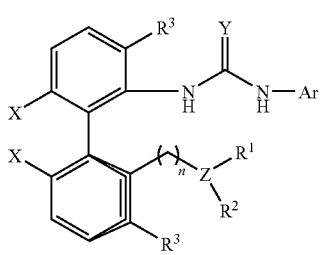

VI

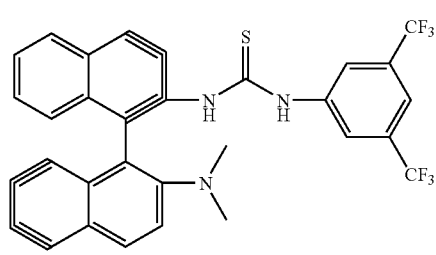

VII

Where Y is O or S;
Z is N or P;
n is 0-6;
$R^1$ and $R^2$ are independently H, an optionally substituted $C_1$-$C_{10}$ hydrocarbyl group, preferably an alkyl group (preferably, $C_1$-$C_8$ alkyl) or a three- to seven-membered optionally substituted heterocyclic group or together with the nitrogen to which they are attached, $R^1$ and $R^2$ form a five or six membered heterocyclic ring;
$R^3$ is H, halogen (F, Cl, Br, I, preferably F), CN, $NO_2$, a $CO_2R$ group, wherein R is an optionally substituted aromatic (preferably phenyl), including a heteroaromatic group, or an optionally substituted $C_1$-$C_6$ alkyl group (preferably substituted with F);
Ar is an optionally substituted aromatic group (preferably, phenyl), including an optionally heteroaromatic group;
X is an optionally substituted aromatic, including an optionally substituted heteroaromatic group, $OR^4$ or $N(R^4)_2$, where each $R^4$ is independently an optionally substituted $C_1$-$C_6$ alkyl group, an optionally substituted $C_3$-$C_7$ carbocyclic group, an optionally substituted aromatic group or a 3- to 7-membered heterocyclic group, or a salt thereof.

In preferred aspects of the invention, $R^1$ and $R^2$ are alkyl groups, preferably a $C_1$-$C_3$ alkyl group, more preferably a methyl group. Y is preferably S, n is 0 or 1 and Z is N. Ar is preferably a phenyl group optionally substituted with an electron withdrawing group preferably selected from $CF_3$, $CF_2CF_3$, F, Cl, Br, I, CN or $NO_2$. $R^3$ is preferably $CF_3$, F, CN or $NO_2$. X is preferably an optionally substituted phenyl group (preferably substituted with an electron withdrawing group selected from $CF_3$, $CF_2CF_3$, F, Cl, Br, I, CN or $NO_2$.

The present invention also relates to methods of synthesizing chemical compounds stereoselectively. Two methods of chemical synthesis using the present organic catalysts are presented herein. The methods are directed to a Morita-Baylis-Hillman reaction to provide chiral alcohols in high efficiency. The first reaction involves the reaction of a nucleophile (in preferred embodiments a 1,3 diketone) to a nitroalkene, such as β-nitrostyrene in the presence of at least one organocatalyst as otherwise described herein to produce an enatiomerically enriched chiral intermediate containing a nitro group (Michael adduct). The Michael adduct can be readily converted into α-substituted-β-amino acid and related compounds. In the second reaction, a 1,4-enone system is reacted with an aldehyde or ketone (preferably an aldehyde) to stereoselectively produce a chiral alcohol in high yield and enantiomeric enrichment (at least about 60% ee, at least about 65% ee, at least about 70% ee, at least about 80%, at least about 85%, at least about 90%, at least about 95%, at least about 97%, at least about 99%, at least about 99+%).)

In the first method, a 1,3-diketone compound according to the formula:

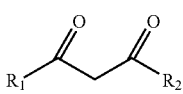

is reacted in a solvent at ambient temperature or at a temperature above or below ambient temperature in the presence of an effective amount of an organocatalyst according to structures I-VII as otherwise described herein with a compound according to the formula:

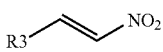

To produce an enatiomerically enriched chiral Michael adduct of the formula:

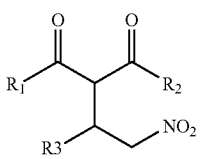

Where $R_1$ and $R_2$ are each independently optionally substituted $C_1$-$C_{12}$ hydrocarbyl groups, preferably alkyl groups, preferably optionally substituted $C_1$-$C_6$ alkyl groups, or an optionally substituted aromatic group, preferably a phenyl group (preferably $R_1$ and $R_2$ are both methyl groups);
$R_3$ is an optionally substituted $C_1$-$C_{12}$ hydrocarbyl group, which is saturated or unsaturated, preferably a $C_1$-$C_6$ alkyl group, more preferably an optionally substituted phenyl group (phenyl or p-hydroxyphenyl are the preferred $R_3$ groups), or a side chain of a naturally occurring amino acid other than an alkyl group which is optionally protected (e.g., a thioether (methionine), an alkylene thiol (cysteine), an alkylene amine (lysine), an alkylene indole group (tryptophan), a —$(CH_2)_3$—NH—C(=NH)$NH_2$ (arginine), a $CH_2OH$ group (serine), an alkylenecarboxamide (asparagine, glutamine), an alkylenecarboxylic acid (aspartic acid, glutamic acid), benzyl (phenylalanine), p-hydroxybenzyl (tyrosine), alkylene imidazole (histidine), among others.

The above reaction is represented schematically as:

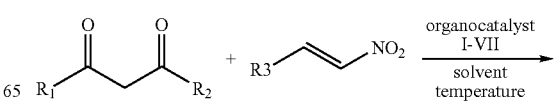

-continued

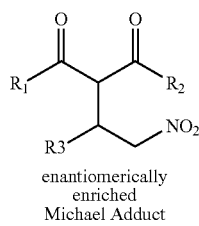

enantiomerically
enriched
Michael Adduct

The product produced by the above reaction is an enatiomerically enriched product:

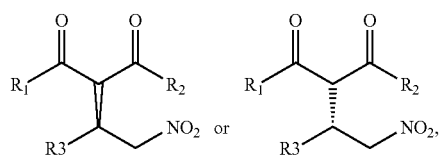

preferably, an enatiomerically enriched compound

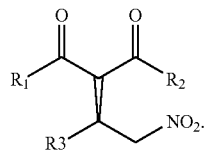

In preferred aspects of the above reaction, both $R_1$ and $R_2$ are the same and preferably both $R_1$ and $R_2$ are methyl groups. The preferred catalyst is the catalyst of formula VII.

The resulting Michael adduct containing the nitro group (preferably where both $R_1$ and $R_2$) are the same may be subjected to a series of facile reactions involving converting the diketo group to a diol group via a procedure first converting the diketone to a keto-ester (using appropriate conditions, such as a Bayer-Villager reaction), reducing the keto-ester to a vicinyl diol, subjecting the vicinyl diol compound to a permanganate/periodate oxidation to cleave the diol and the resulting carboxylic acid compound containing a nitro group produced is exposed to a reducing agent to reduce the nitro group to an amino group, resulting in an α-substituted-β-amino acid according to the structure:

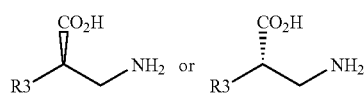

Where $R_3$ is the same as described above. In the final product $R_3$ is preferably an unprotected group.

In a second method, a compound having a 1,4-enone system is reacted with an aldehyde or ketone in the presence of solvent, catalyst according to the present invention at a temperature optionally above or below ambient temperature to produce a chiral allylic alcohol.

In this method to produce an enantiomerically enriched chiral allylic alcohol, a compound according to structure:

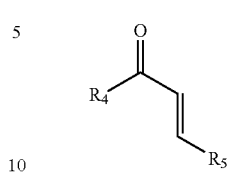

is reacted in a solvent at ambient temperature or optionally at a temperature above or below ambient temperature in the presence of an effective amount of an organocatalyst according to the present invention with a compound according to the structure:

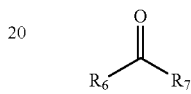

Where $R_4$ is selected from H, an optionally substituted $C_1$-$C_{12}$ hydrocarbyl group, preferably an optionally substituted alkyl group or $R_4$ and $R_5$ are linked to form a 5- to 7-membered (preferably a 6-membered) carbocyclic group with the moieties to which they are attached;

$R^5$ is an optionally substituted $C_1$-$C_{12}$ hydrocarbyl group which is optionally unsaturated, and is preferably an alkyl group or together with $R^4$, forms a carbocyclic group with the moieties to which they are attached;

$R_6$ is H or an optionally substituted $C_1$-$C_{12}$ hydrocarbyl group which is saturated or unsaturated, preferably a phenyl or substituted (included alkylene) phenyl such as benzyl, or an optionally substituted alkyl or alkene group; and $R_7$ is an optionally substituted $C_1$-$C_{12}$ hydrocarbyl group which is saturated or unsaturated, preferably a phenyl or substituted (included alkylene) phenyl such as benzyl, or an optionally substituted alkyl or alkene group to produce an enantiomerically enriched chiral allylic alcohol compound according to the structure:

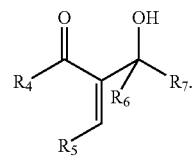

The product produced by the above reaction is an enatiomerically product

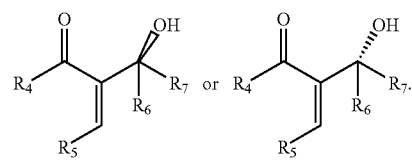

In the initial study, six organocatalysts were screened for the process (Figure 1 and Table 1). They include compounds A-E, which have been used for catalyzing various reactions[8-11] and the newly designed VII.[13] A reaction between 2,4-pentandione 1 and trans-β-nitrostyrene 2a in THF at rt in the presence of catalyst (10 mol %) was used to evaluate their catalytic activities. The results showed that catalysts A-C exhibited poor activities, in contrast, thioureas D, E, and VII afforded the promising results. Under the same reaction conditions, catalyst D gave the product 3a in high enantioselectivity (96% ee), but it took a long reaction time. The E-catalyzed process was accomplished in a much shorter time, whereas a lower enantioselectivity was observed. In comparison, the new organocatalyst VII proved to be of the choice for further investigation. In this instance, not only did the reaction proceed to completion within 3.5 h, but a high reaction yield (93%) and enantioselectivity (95% ee) were achieved as well.

TABLE 1

Results of organocatalyst screening for asymmetric Michael addition reactions of 2,4-pentanedione (1a) and trans-β-nitrostyrene (2a)[a]

| entry | catalyst | t (h) | % yield[b] | % ee[c] |
|---|---|---|---|---|
| 1 | A | 60 | <10 | n.d.[d] |
| 2 | B | 30 | <10 | n.d.[d] |
| 2 | C | 48 | 52 (90)[e] | 17 |
| 3 | D | 48 | 47 (95)[e] | 96 |
| 4 | E | 8 | 92 | 84 |
| 5 | VII | 3.5 | 93 | 95 |

[a]Reaction conditions: see Experimental Section.
[b]Isolated yields.
[c]Enantiomeric excess (ee) deteremined by chiral HPLC analysis (Chiralpak AS-H).
[d]Not deteremined.
[e]Yields based on recovered staring materials.

A survey of 9 solvents reveals that a variety of solvents are tolerant of this Michael addition reaction.[14] Generally, in polar solvents such as DMSO (Table 2, entry 6), almost no enantioselectivity for product 3a was observed probably because of the destruction of hydrogen bonding interactions between the thiourea and the nitro group in the substrate by strong polar solvents. As expected, when reactions were conducted in less polar solvents, high enantioselectivities were obtained (entries 1-5). With Et$_2$O as solvent, the Michael adduct 3a was isolated with the highest ee (97%) in 95% yield (entry 3). Further optimization of this process showed that the reaction can be performed with as low as 1 mol % catalyst loading (entry 5). A comparable result (95% ee, 87% yield) was achieved without significant sacrificing reaction time.

TABLE 2

Optimization reaction conditions of the asymmetric Michael addition of 2,4-pentanedione 1a and trans-β-nitrostyrene 2.[a]

| entry | solvent | t (h) | % yield[b] | % ee[c] |
|---|---|---|---|---|
| 1 | THF | 3.5 | 93 | 95] |
| 2 | toluene | 7.0 | 89 | 91 |
| 3 | Et$_2$O | 5.0 | 95 | 97 |
| 4[d] | Et$_2$O | 15.0 | 92 | 95 |
| 5[e] | Et$_2$O | 28.0 | 95 | 95 |
| 6 | DMSO | 2.0 | 96 | 5 |

[a]Reaction condition: see Experimental Section.
[b]Isolated yields.
[c]Ee deteremined by chiral HPLC analysis (Chiralpak AS-H).
[d]2 mol % catalyst used.
[e]1 mol % catalyst used.

Figure 3:
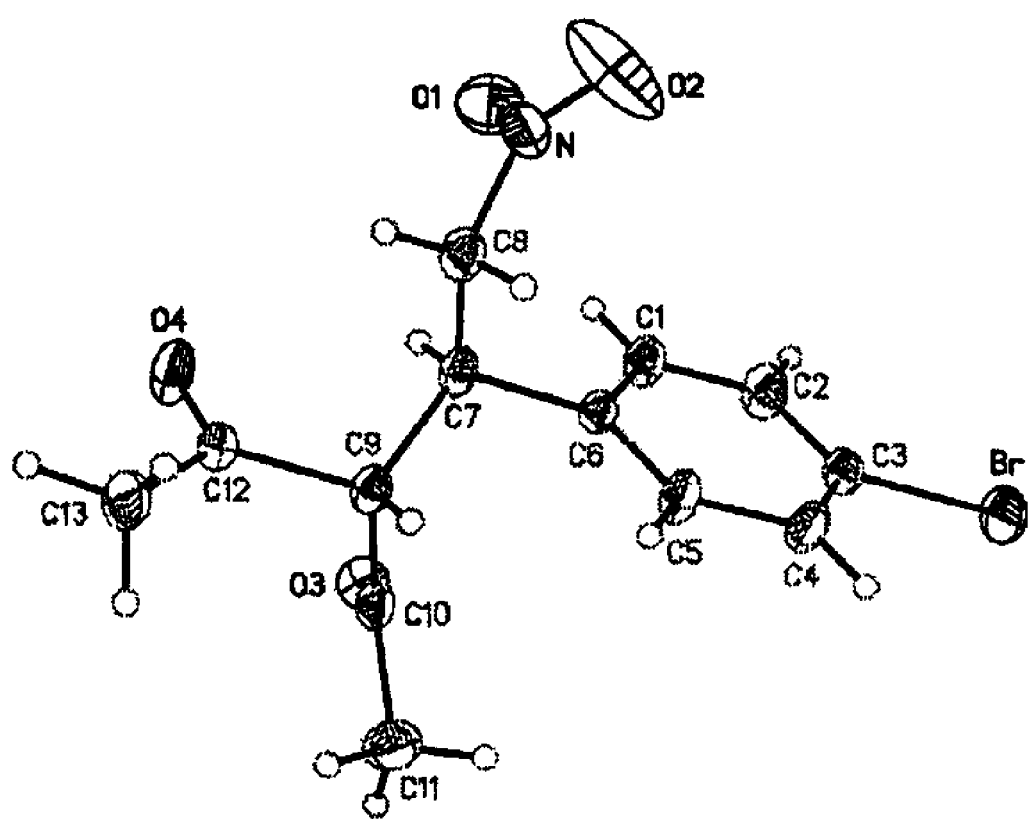
FIG. 3 shows the X-ray crystallography of compound 3f to determine its absolute configuration.

With optimized reaction conditions in hand, the scope of the reaction was explored (Table 3). The Michael addition reaction of 2,4-pentanedione 1 with a variety of nitroolefins 2 was probed. The results showed, in general, that the reactions took place efficiently (78-92%), and high to excellent levels of enantioselectivity (80-97% ee) with all of nitroolefins tested were achieved. As revealed by inspecting the results given in Table 3, the processes were applicable to nitroolefins bearing electron-withdrawing (Table 3, entries 5, 6 and 9) and electron-donating substituents (entries 1-4, 7-8, 10-13). The absolute configuration of 3f was determined by X-ray crystallography to be S (figure 3).

TABLE 3

Catalyst VII catalyzed Michael addition reactions of aldehydes to trans-β-nitrostyrenes.

| entry | Ar | adduct | time (h) | % yield[a] | % ee[b] |
|---|---|---|---|---|---|
| 1 | Ph | 3a | 26 | 87 | 95 |
| 2 | 4-Me—C$_6$H$_4$ | 3b | 36 | 84 | 93 |

TABLE 3-continued

Catalyst VII catalyzed Michael addition reactions of aldehydes to trans-β-nitrostyrenes.

| entry | Ar | adduct | time (h) | % yield[a] | % ee[b] |
|---|---|---|---|---|---|
| 3 | 4-MeO—$C_6H_4$ | 3c | 36 | 92 | 97 |
| 4 | 4-BnO—$C_6H_4$ | 3d | 26 | 90 | 94 |
| 5 | 4-Cl—$C_6H_4$ | 3e | 24 | 91 | 97 |
| 6 | 4-Br—$C_6H_4$ | 3f | 27 | 89 | 95 |
| 7 | 2-BnO—$C_6H_4$ | 3g | 48 | 80 | 89 |
| 8 | 2-MeO—$C_6H_4$ | 3h | 30 | 92 | 97 |
| 9 | 2-$CF_3$—$C_6H_4$ | 3i | 24 | 86 | 83 |
| 10 | 2,4-$(MeO)_2$—$C_6H_3$ | 3j | 36 | 88 | 91 |
| 11 | 3-BnO-4-MeO—$C_6H_3$ | 3k | 60 | 78 | 88 |
| 12 | 2,3-$(MeO)_2$—$C_6H_3$ | 3l | 36 | 87 | 92 |
| 13 | 3,4-$(OCH_2)O)$—$C_6H_3$ | 3m | 36 | 91 | 80 |

[a]Isolated yields.
[b]Deteremined by chiral HPLC analysis (Chiralpak AS-H, or AD and Chiralcel OD-H).

The Michael adducts can be employed for the efficient preparation of α-substituted β-amino acids (Scheme 1). Note that $R_3$ is limited to a phenyl group in this example, although a large number of other groups may be utilized here. Compound 3a was converted into α-acetoxyketone 5 by Bayer-Villiger oxidation, and subsequent reduction provided corresponding diol 6. Following the cleavage of the diol by sodium periodate and hydrogenation with Pd/C gave α-phenyl-β-alanine 4a ($[\alpha]^{25}_D$=+88.2, c=0.5, $H_2O$, lit.[15]: $[\alpha]^{25}_D$=+85, c=0.2, $H_2O$) in a 38% overall yield.

Scheme 1. Representative Synthesis of α-phenyl-β-alanine 4a.

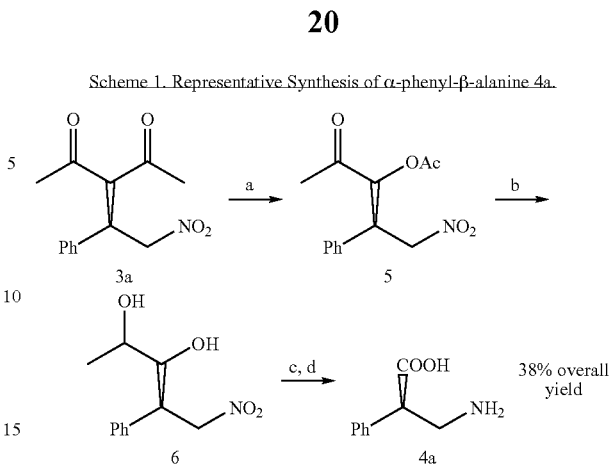

(a) oxone, $K_2CO_3$, acetone/$CH_2Cl_2$/$H_2O$, 0° C. (b) DIBAL-H, toluene, −78° C. (c) cat. $KMnO_4$, $NaIO_4$, $Na_2CO_3$, 1,4-dioxane/$H_2O$, 23° C. (d) $H_2$, Pd/C, 50 psi, MeOH.

Catalysts according to the present invention, especially the bifunctional binaphthyl-derived amine thiourea VII, serves as an efficient organocatalyst for asymmetric Michael addition of 1,3-diketone to nitroolefins. In this investigation, we have demonstrated the first highly enantioselective Michael reaction of 1,3-diketones as donors with β-nitrostyrenes. Notably, the utilization of the catalyst VII as low as 1 mol % is sufficient for the process. Moreover, the Michael addition products can be readily converted into valuable building blocks α-substituted-β-amino acids.

Thiourea-based organocatalysts have been widely used for effective activation of carbonyls, imines, and nitro groups through efficient double hydrogen-bonding interactions.[5a,6a] We envisioned that appropriately positioning a thiourea and a tertiary amine in a chiral scaffold could result in a new type of bifunctional organocatalyst. The thiourea group would serve as an acid to activate a carbonyl group in α, β-unsaturated systems, and, subsequently, facilitate the Michael addition of the tertiary amine to the β-position of the substrate (Scheme 1). Two well studied chiral scaffolds, trans-cyclohexane diamine and binaphthyl diamine, were selected for harboring the thiourea and amine moieties (figure 2).[7a] Compound I has been used previously for Michael addition[6ah,ai,ak] and aza-Henry[6aj] reactions, whereas binaphthyl-derived amine thioureas VII and A-D are first proposed here as organocatalysts for promoting asymmetric transformations. They were readily synthesized from commercially available R-binaphthyl diamine (see the supporting information).

Scheme 1. Proposed catalytic cycle for amine-thiourea promoted MBH reaction.

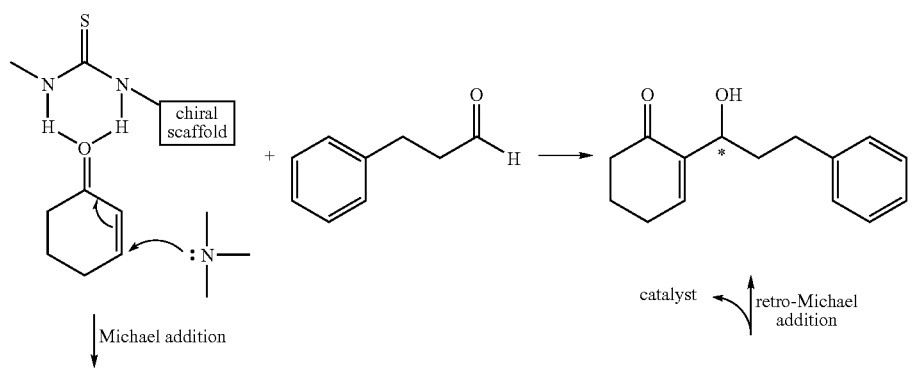

-continued

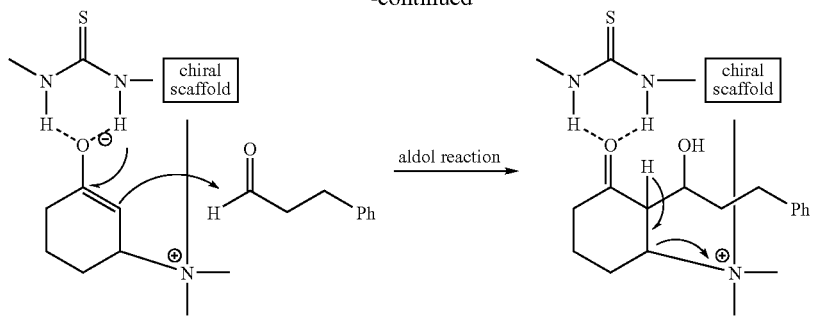

Figure 2:
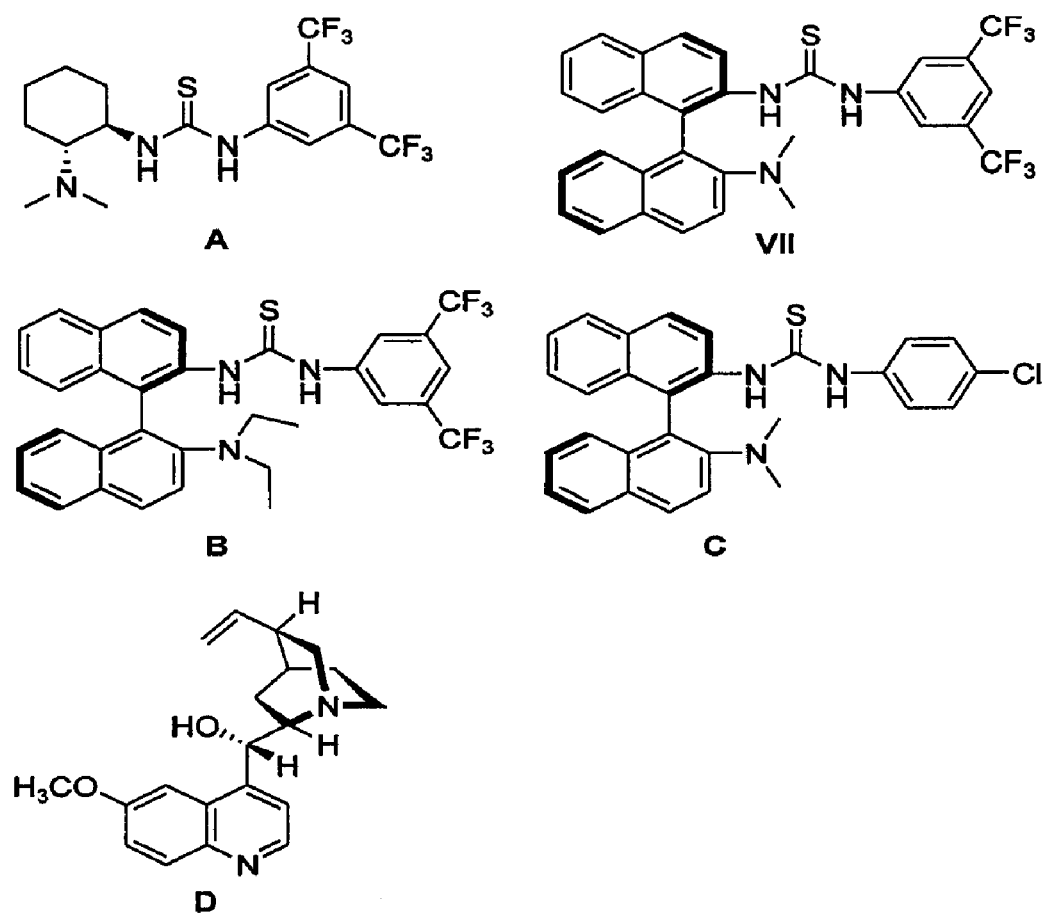
FIG. 2 shows exemplary catalysts and compounds according to the present invention.

An exploratory study using a model reaction of 2-cyclohexen-1-one 1a with 3-phenylpropionaldehyde 2a in the presence of 10 mol % catalyst in CH$_2$Cl$_2$ at room temperature was conducted to determine the catalytic ability of bifunctional organocatalysts VII and A-D (figure 2 and Table 1). Examination of the results revealed that their catalytic activities varied significantly. Cyclohexanediamine-derived amine thiourea I, which provided high enantioselectivities for the Michael addition[6h,i,k] and aza-Henry reactions,[6j] showed poor activity toward the MBH reaction. Low reaction yield (21%) and low enantioselectivity (39% ee) were observed (Table 1, entry 1). The newly designed binaphthyl amine thiourea VII afforded the most promising catalytic capacity in terms of reaction yield (83%) and enantioselectivity (71% ee) (Table 1, entry 2). The more bulky analogue B displayed similar enantioselectivity (73% ee), but gave a lower yield (56%) (entry 3) in this exploring screening. Catalyst C showed only low catalytic activity in the MBH reaction (18% yield, entry 4). The significant difference in catalyst activities among VII and B, C is presumably due to the stronger H-bonding interaction with the carbonyl group of cyclohexenone 1a, imposed by 3,5-bistrifluoromethane phenyl in VII and B over p-Cl phenyl group in CV.[8a] The catalytic activity of bifunctional cinchona alkaloid D was also evaluated and turned out to be poor (<10% yield) after 48 h (entry 5).

TABLE 1

Optimization reaction conditions of catalytic asymmetric Baylis-Hillman reactions of 2-cyclohexen-1-one (1a) with 3-phenylpropionaldehyde (2a)[a]

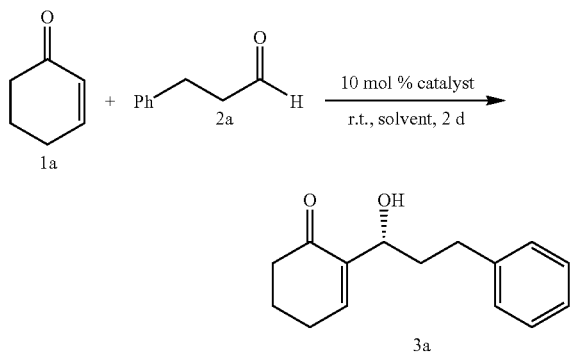

| entry | catalyst | solvent | % yield[b] | % ee[c] |
|---|---|---|---|---|
| 1 | A | CH$_2$Cl$_2$ | 21 | 39 |
| 2 | VII | CH$_2$Cl$_2$ | 83 | 71 |
| 3 | B | CH$_2$Cl$_2$ | 56 | 73 |
| 4 | C | CH$_2$Cl$_2$ | 18 | n.d.[e] |
| 5 | D | CH$_2$Cl$_2$ | <10 | n.d.[e] |
| 6 | VII | toluene | 80 | 77 |

TABLE 1-continued

Optimization reaction conditions of catalytic asymmetric Baylis-Hillman reactions of 2-cyclohexen-1-one (1a) with 3-phenylpropionaldehyde (2a)[a]

| entry | catalyst | solvent | % yield[b] | % ee[c] |
|---|---|---|---|---|
| 7[d] | VII | toluene | 63 | 80 |
| 8 | VII | CH$_3$CN | 83 | 80 |
| 9[d] | VII | CH$_3$CN | 80 | 83 |
| 10 | VII | Et$_2$O | 82 | 77 |
| 11[d] | VII | Et$_2$O | 72 | 73 |
| 12 | VII | DMSO | 47 | 70 |

[a]Unless otherwise specified, the reaction was carried out with 2 equiv. of 1a and 1 equiv. of 2a in the presence of 10 mol % catalyst in CH$_2$Cl$_2$ for 2 d.
[b]Isolated yields.
[c]Enantiomeric excess (ee) determined by chiral HPLC analysis (Chiralcel OD-H).
[d]at 0° C.
[e]Not determined.

Solvent effects on this process using VII as the organocatalyst were probed next (Table 1, entries 6-12).[9a] The results showed that a variety of solvents can be employed for the VII catalyzed MBH reaction. The better results were provided when the reactions were performed in toluene (80% yield, 77% ee, entry 6), CH$_3$CN (83% yield, 80% ee, entry 8), and Et$_2$O (82% yield, 77% ee, entry 10) in the presence of 10 mol % VII at room temperature. Encouraged by these results, we studied the effects of temperature on the reaction in these three solvents. Lowering the temperature to 0° C. resulted in improving enantioselectivities without significantly sacrificing reaction yields (Table 1, entries 7, 9 and 10). In more polar media, such as DMSO, the reaction proceeded slowly (47% yield, entry 12). These studies prompted us to select the reaction conditions using CH$_3$CN as solvent at 0° C. in the presence of 10 mol % VII to probe the scope of the MBH reactions.

Reactions of 2-cyclohexen-1-one 1a with various aldehydes 2 were carried out under the optimized reaction conditions. As the results summarized in Table 2 show, the reactions proceeded smoothly to generate chiral allylic alcohols 3 in good yields (63-84%) and high to excellent enantioselectivities (80-94% ee). The absolute configurations of the MBH reaction products were determined by comparison with optical rotation studies of known compounds.[2c] Regardless of the length of linear aliphatic aldehydes 2, in every case, high enantioselectivities (80-83% ee) and good to high yields (71-84%, entries 1-7) were achieved. More significantly, the more sterically demanding aldehydes gave allylic alcohols with excellent enantioselectivities (90-94% ee) and good yields (63-71%, entries 8-10).

TABLE 2

Catalyst VII catalyzed Baylis-Hillman reactions of 2-cyclohexen-1-one with aldehydes[a]

| entry | product | Time (h) | % yield[b] | % ee[c] |
|---|---|---|---|---|
| 1 | (CH₂CH₂Ph) | 48 | 80 | 83 |
| 2 | (CH₂CH(CH₃)₂) | 72 | 72 | 80 |
| 3 | n-C₄H₉ | 48 | 84 | 81 |
| 4 | n-C₅H₁₁ | 60 | 75 | 81 |
| 5 | n-C₆H₁₃ | 72 | 71 | 80 |
| 6 | n-C₇H₁₅ | 72 | 74 | 82 |
| 7 | (CH₂CH₂CH=CHCH₂CH₃) | 72 | 82 | 81 |
| 8 | iPr | 72 | 63 | 94 |
| 9 | cyclopentyl | 96 | 71 | 90 |
| 10 | cyclohexyl | 120 | 67 | 92 |

[a] Unless otherwise specified, see the footnote a in Table 1.
[b] Isolated yields.
[c] Determined by chiral HPLC analysis (Chiralpak AS-H, or Chiralcel OD-H).

In summary, the investigation described above has resulted in identifying a novel chiral amine-thiourea bifunctional organocatalyst VII. It has been demonstrated to promote the asymmetric MBH reactions of cyclohexenone with a verity of aldehydes to afford highly functionalized, synthetically useful chiral allylic alcohols. In this process, VII exhibits high catalytic activity and good to excellent levels of enantioselectivity toward this reaction. Other aspects of the invention focus on improving the catalyst activity and reaction enantioselectivity and probing the full scope of the reaction.

EXAMPLES

The following examples are presented to assist the reader in understanding the present invention. The exemplary subject matter presented below should not be construed to limit the scope of the invention in any way.

(R)—N-(1-(2-aminonaphthalen-1-yl)naphthalen-2-yl)acetamide (1). To a solution of (R)-(+)-1,1'-Binaphthyl-2,2'-diamine (284 mg, 1.0 mmol) and AcOH (0.6 mL, 10 mmol) in 10 mL of dried $CH_2Cl_2$ was added acetic anhydride (104 μL, 1.0 mmol) at 0° C. under $N_2$. The resulting solution was stirred for overnight at room temperature, then 2N NaOH aqueous solution was added until pH≈7. The organic layer was dried over $MgSO_4$, and concentrated in vacuo. Flash chromatography (Ethyl Acetate/Hexane=2/1) afforded a colorless oil in 77% yield (0.25 g, 0.77 mmol). $^1$H NMR (500 MHz, $CDCl_3$, TMS): δ=8.23 (dd, 1H, J=8.0, 4.5 Hz), 7.99 (d, 1H, J=9.0 Hz), 7.90 (d, 1H, J=8.0 Hz), 7.85 (d, 1H, J=9.0 Hz), 7.81 (d, 1H, J=8.0 Hz), 7.40 (t, 1H, J=9.0 Hz), 7.27-7.12 (m, 6H), 7.04 (s, 1H), 6.91 (d, 1H, J=8.0 Hz), 3.65 (s, 2H), 1.84 (s, 3H); $^{13}$C NMR (125 MHz, $CDCl_3$, TMS): δ=168.7, 142.7, 135.0, 134.9, 133.5, 132.3, 131.2, 130.3, 129.2, 128.2, 128.1, 127.3, 126.8, 125.4, 125.1, 123.6, 122.9, 122.7, 120.8, 118.0, 110.3, 24.6.

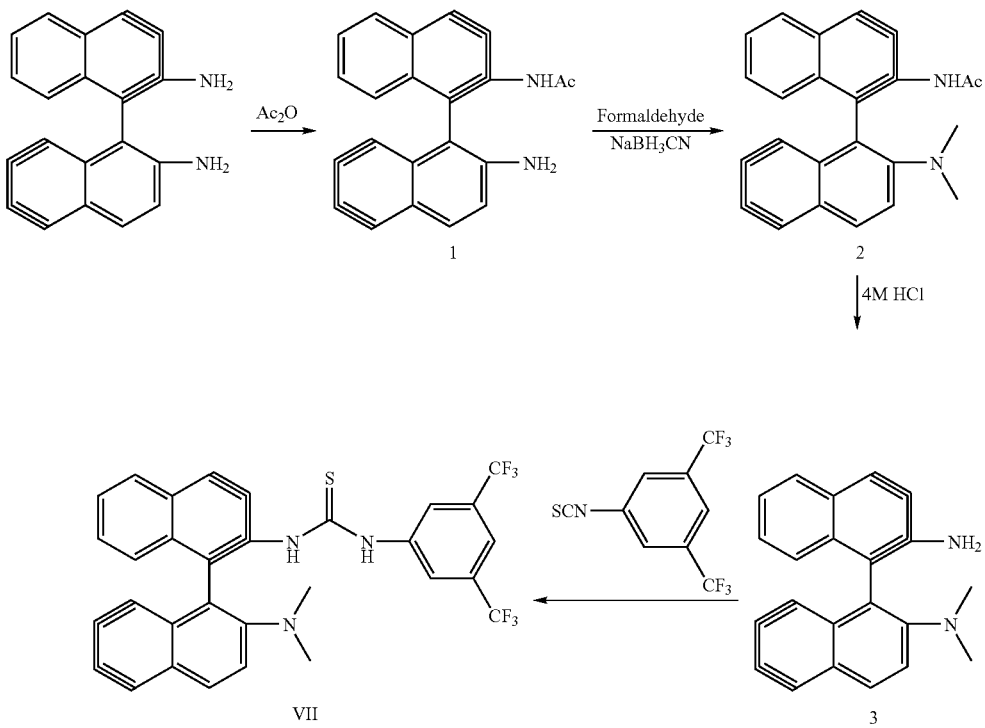

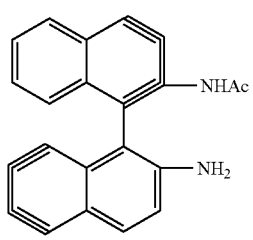

FIGURE. Synthesis of binapthal-based thiourea catalyst VII.

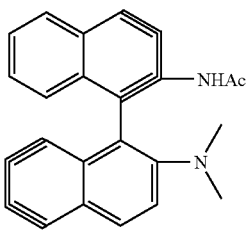

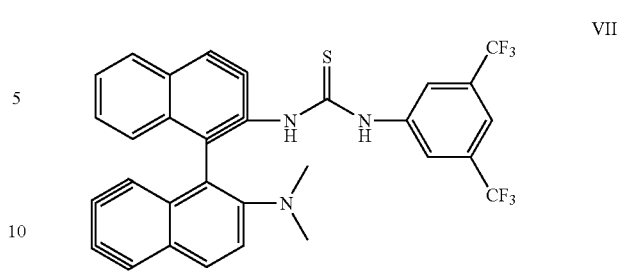

(R)—N-(1-(2-(dimethylamino)naphthalen-1-yl)naphthalen-2-yl)acetamide (2). N-(1-(2-aminonaphthalen-1-yl)naphthalen-2-yl)acetamide 1 (0.25 g, 0.77 mmol) and aqueous formaldehyde (37%, 0.75 ml, 9.0 mmol) were combined in 10 mL of THF and stirred for 15 min. NaBH$_3$CN (200 mg, 5.3 mmol) was added, followed 15 min later by AcOH (1.0 ml). The resulting solution was stirred for 4 h at room temperature, then 1N NaOH aqueous solution was added until pH≈7. The organic layer was dried over MgSO$_4$, and concentrated in vacuo. Flash chromatography (Ethyl Acetate/Hexane=1/5) afforded a brown powder in quantitative yield (272 mg, 0.77 mmol). $^1$H NMR (500 MHz, CDCl$_3$, TMS): δ=8.48 (d, 1H, J=9.0 Hz), 7.96 (d, 2H, J=8.5 Hz), 7.88 (d, 2H, J=8.0 Hz), 7.83 (d, 2H, J=8.0 Hz), 7.53 (s, 1H), 7.49 (d, 2H, J=9.0 Hz), 7.38 (t, 2H, J=8.0 Hz), 7.31 (d, 2H, J=7.0 Hz), 7.22 (d, 2H, J=7.0 Hz), 7.16-7.11 (m, 2H), 6.93 (d, 2H, J=8.5 Hz), 2.65 (s, 6H), 1.86 (s, 3H); $^{13}$C NMR (125 MHz, CDCl$_3$, TMS): δ=169.2, 149.5, 133.6, 133.4, 131.2, 130.1, 129.7, 128.6, 128.2, 127.9, 126.8, 126.5, 126.4, 125.3, 125.0, 124.1, 121.8, 121.5, 118.6, 118.0, 48.6, 43.4, 24.4.

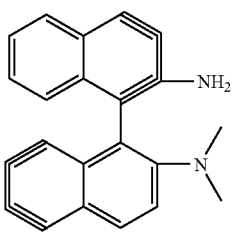

(R)-1-(2-(dimethylamino)naphthalen-1-yl)naphthalen-2-amine (3). A solution of N-(1-(2-(dimethylamino)naphthalen-1-yl)naphthalen-2-yl)acetamide 2 (0.18 g, 0.51 mmol) in 15 mL of EtOH was added 4M HCl (6 mL). The resulting solution was stirred for overnight at room temperature, then 1N NaOH aqueous solution was added until pH≈7. The organic layer was dried over MgSO$_4$, and concentrated in vacuo. Flash chromatography (Ethyl Acetate/Hexane=1/10) afforded a colorless oil in 93% yield (148 mg, 0.47 mmol). $^1$H NMR (500 MHz, CDCl$_3$, TMS): δ=7.90 (d, 2H, J=9.0 Hz), 7.81 (d, 2H, J=8.0 Hz), 7.77 (d, 2H, J=8.0 Hz), 7.47 (d, 1H, J=9.0 Hz), 7.29-7.10 (m, 6H), 7.02 (d, 1H, J=8.5 Hz), 3.67 (s, 1H), 2.59 (s, 6H); $^{13}$C NMR (125 MHz, CDCl$_3$, TMS): δ=150.4, 141.8, 134.2, 133.7, 129.7, 129.1, 128.8, 128.3, 127.9, 127.8, 126.5, 126.2, 124.9, 123.6, 122.1, 121.9, 119.5, 118.4, 116.8, 43.3.

(R)-1-(3,5-bis(trifluoromethyl)phenyl)-3-(1-(2-(dimethylamino)naphthalen-1-yl)naphthalen-2-yl)thiourea (VII). To a solution of 1-(2-(dimethylamino)naphthalen-1-yl)naphthalen-2-amine 3 (36 mg, 0.12 mmol) in 2 mL of dried CH$_2$Cl$_2$ was added 3,5-bis(trifluoromethyl)phenyl isothiocyanate (22 mg, 0.132 mmol) at 0° C. under N$_2$. The resulting solution was stirred for overnight at room temperature. Flash chromatography (Ethyl Acetate/Hexane=1/10) afforded a slight yellow solid in 91% yield (64 mg, 0.11 mmol). $[α]^{25}_D$=−8.3 (c=0.5 in CHCl$_3$); $^1$H NMR (500 MHz, CDCl$_3$, TMS): δ=8.37 (s, 1H), 8.06 (d, 1H, J=8.5 Hz), 7.98 (d, 2H, J=9.0 Hz), 7.82 (d, 1H, J=8.0 Hz), 7.71 (d, 1H, J=8.5 Hz), 7.56-7.50 (m, 5H), 7.41 (s, 1H), 7.36 (s, 2H), 7.26 (m, 2H), 7.09 (t, 1H, J=7.5 Hz), 6.90 (d, 1H, J=7.5 Hz), 2.59 (s, 6H); $^{13}$C NMR (125 MHz, CDCl$_3$, TMS): δ=179.7, 149.9, 139.6, 134.0, 133.3, 133.2, 132.9, 132.0, 131.8, 131.6, 130.5, 130.0, 129.9, 128.5, 128.4, 127.5, 127.2, 126.8, 125.0, 124.6, 124.2, 123.9, 122.9, 121.8, 118.9, 44.0.

Typical Procedure for Michael Addition Reaction: The catalyst amino-thiourea VII (1 mg, 0.0017 mmol) was added to a vial containing 2,4-pentanedione 1a (38 μl, 0.34 mmol) and trans-β-nitrostyrene 2a (26 mg, 0.17 mmol) in Et$_2$O (1 mL) at room temperature. After 28 h of stirring, TLC analysis indicated completion of the reaction. The reaction mixture was concentrated in vacuo. The residue was purified by flash silica gel chromatography (ethyl acetate/hexane=1:10 to 1:3) to afford 37 mg (87%) of the adduct as a white solid. Absolute configuration of the products was determined by X-ray crystallography.

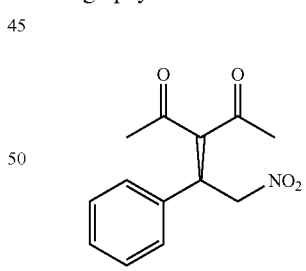

3-((R)-2-nitro-1-phenylethyl)pentane-2,4-dione (Table 3, entry 1): The title compound was prepared according the typical procedure, as described above in 87% yield. $^1$H NMR (500 MHz, CDCl$_3$, TMS): δ=7.35-7.26 (m, 3H; Ph), 7.21-7.16 (m, 2H; Ph), 4.68-4.59 (m, 2H; CH$_2$), 4.38 (d, J=10.5 Hz, 1H; CH), 4.28-4.21 (m, 1H; CH), 2.30 (s, 3H; CH$_3$), 1.95 (s, 3H; CH$_3$); $^{13}$C NMR (125 MHz, CDCl$_3$, TMS): δ=201.7, 201.0, 135.9, 129.3, 128.5, 127.9, 78.2, 70.7, 42.7, 30.4, 29.5; HPLC (Chiralpak AS-H, i-Propanol/Hexane=15/85, flow rate 1.0 mL/min, λ=210 nm): $t_{minor}$=14.5 min, $t_{major}$=23.9 min, ee=95%; $[α]^{25}_D$(major)=−147.6° (c=3.0 in CHCl$_3$).

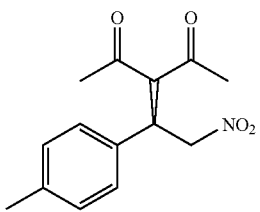

3-((R)-2-nitro-1-p-tolylethyl)pentane-2,4-dione (Table 3, entry 2): The title compound was prepared according the typical procedure, as described above in 84% yield. $^1$H NMR (500 MHz, CDCl$_3$, TMS): δ=7.12 (d, J=8.0 Hz, 2H; Ph), 7.06 (d, J=8.0 Hz, 2H; Ph), 4.65-4.57 (m, 2H; CH$_2$), 4.36 (d, J=11.0 Hz, 1H; CH), 4.24-4.17 (m, 1H; CH), 2.30 (s, 3H; CH$_3$), 2.29 (s, 3H; CH$_3$), 1.94 (s, 3H; CH$_3$); $^{13}$C NMR (125 MHz, CDCl$_3$, TMS): δ=201.9, 201.1, 138.3, 132.7, 130.0, 127.7, 78.3, 70.8, 42.4, 30.4, 29.4, 21.0; HPLC (Chiralpak AS-H, i-Propanol/Hexane=15/85, flow rate 1.0 mL/min, λ=210 nm): t$_{minor}$=11.8 min, t$_{major}$=18.8 min, ee=93%; [α]$^{25}_D$(major)=−71.9° (c=3.0 in CHCl$_3$).

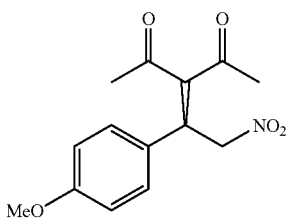

3-((R)-1-(4-methoxyphenyl)-2-nitroethyl)pentane-2,4-dione (Table 3, entry 3): The title compound was prepared according the typical procedure, as described above in 92% yield. $^1$H NMR (500 MHz, CDCl$_3$, TMS): δ=7.10 (d, J=8.5 Hz, 2H; Ph), 6.84 (d, J=8.5 Hz, 2H; Ph), 4.61-4.57 (m, 2H; CH$_2$), 4.35 (d, J=11.0 Hz, 1H; CH), 4.24-4.18 (m, 1H; CH), 3.78 (s, 3H; OCH$_3$), 2.29 (s, 3H; CH$_3$), 1.95 (s, 3H; CH$_3$); $^{13}$C NMR (125 MHz, CDCl$_3$, TMS): δ=201.8, 201.1, 159.4, 129.0, 127.5, 114.6, 78.4, 70.8, 55.1, 42.0, 30.3, 29.4; HPLC (Chiralpak AD, i-Propanol/Hexane=20/80, flow rate 0.8 mL/min, λ=210 nm): t$_{minor}$=11.0 min, t$_{major}$=15.2 min, ee=97%; [α]$^{25}_D$(major)=−108.3° (c=2.7 in CHCl$_3$).

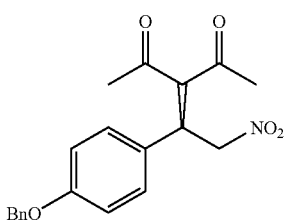

3-((R)-1-(4-(benzyloxy)phenyl)-2-nitroethyl)pentane-2,4-dione (Table 3, entry 4): The title compound was prepared according to the typical procedure, as described above in 90% yield. $^1$H NMR (500 MHz, CDCl$_3$, TMS): δ=7.42-7.33 (m, 5H; Ph), 7.10 (d, J=8.5 Hz, 2H; Ph), 6.91 (d, J=8.5 Hz, 2H; Ph), 5.00 (s, 2H; OCH$_2$), 4.62-4.56 (m, 2H; CH), 4.33 (d, J=10.5 Hz, 1H; CH), 4.23-4.16 (m, 1H; CH), 2.29 (s, 3H; CH$_3$), 1.95 (s, 3H; CH$_3$); $^{13}$C NMR (125 MHz, CDCl$_3$, TMS): δ=201.8, 201.1, 158.7, 136.5, 129.1, 128.6, 128.1, 127.9, 127.5, 115.5, 78.4, 70.9, 70.0, 42.1, 30.4, 29.5; HPLC (Chiralpak AD, i-Propanol/Hexane=30/70, flow rate 1.0 mL/min, λ=210 nm): t$_{minor}$=8.9 min, t$_{major}$=11.6 min, ee=94%; [α]$^{25}_D$(major)=−78.8° (c=2.7 in CHCl$_3$).

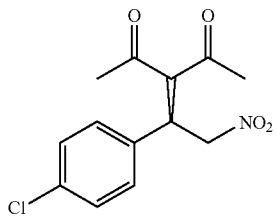

3-((R)-1-(4-chlorophenyl)-2-nitroethyl)pentane-2,4-dione (Table 3, entry 5): The title compound was prepared according the typical procedure, as described above in 91% yield. $^1$H NMR (500 MHz, CDCl$_3$, TMS): δ=7.32 (d, J=8.5 Hz, 2H; Ph), 7.14 (d, J=8.5 Hz, 2H; Ph), 4.65-4.60 (m, 2H; CH$_2$), 4.33 (d, J=11.0 Hz, 1H; CH), 4.27-4.20 (m, 1H; CH), 2.29 (s, 3H; CH$_3$), 1.98 (s, 3H; CH$_3$); $^{13}$C NMR (125 MHz, CDCl$_3$, TMS): δ=201.4, 200.6, 134.5, 129.5, 129.3, 77.9, 70.4, 42.1, 30.4, 29.7; HPLC (Chiralpak AS-H, i-Propanol/Hexane=15/85, flow rate 1.0 mL/min, λ=210 nm): t$_{minor}$=16.5 min, t$_{major}$=34.7 min, ee=97%; [α]$^{25}_D$(major)=89.20 (c=3.0 in CHCl$_3$).

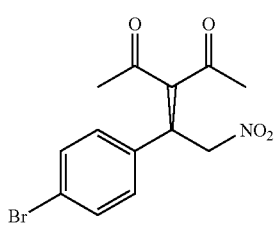

3-((R)-1-(4-bromophenyl)-2-nitroethyl)pentane-2,4-dione (Table 3, entry 6): The title compound was prepared according the typical procedure, as described above in 89% yield. $^1$H NMR (500 MHz, CDCl$_3$, TMS): δ=7.47 (d, J=8.5 Hz, 2H; Ph), 7.08 (d, J=8.5 Hz, 2H; Ph), 4.65-4.58 (m, 2H; CH$_2$), 4.33 (d, J=10.5 Hz, 1H; CH), 4.26-4.19 (m, 1H; CH), 2.29 (s, 3H; CH$_3$), 1.98 (s, 3H; CH$_3$); $^{13}$C NMR (125 MHz, CDCl$_3$, TMS): δ=201.3, 200.5, 135.0, 132.5, 129.6, 122.6, 77.8, 70.4, 42.1, 30.4, 29.7; HPLC (Chiralpak AS-H, i-Propanol/Hexane=15/85, flow rate 1.0 mL/min, λ=210 nm): t$_{minor}$=17.1 min, t$_{major}$=32.3 min, ee=95%; [α]$^{25}_D$(major)=−37.2° (c=1.2 in CHCl$_3$).

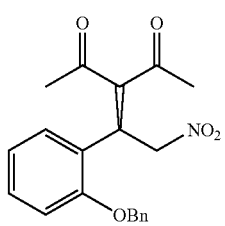

3-((R)-1-(2-(benzyloxy)phenyl)-2-nitroethyl)pentane-2,4-dione (Table 3, entry 7): The title compound was prepared according to the typical procedure, as described above in 80% yield. $^1$H NMR (500 MHz, CDCl$_3$, TMS): δ=7.52-7.35 (m, 5H; Ph), 7.28-7.22 (m, 1H; Ph), 7.10 (dd, J=7.5 Hz, 1.0 Hz, 1H; Ph), 6.96 (d, J=8.0 Hz, 1H; Ph), 6.90 (t, J=7.5 Hz, 1H; Ph), 5.12 (s, 2H; OCH$_2$), 4.80 (dd, J=11.5 Hz, 7.5 Hz, 1H; CH$_2$), 4.58-4.47 (m, 3H; CH, CH$_2$), 2.18 (s, 3H; CH$_3$), 1.91 (s, 3H; CH$_3$); $^{13}$C NMR (125 MHz, CDCl$_3$, TMS): δ=202.2, 201.5, 156.2, 136.3, 130.4, 129.7, 128.8, 128.4, 127.8, 123.6, 121.4, 122.5, 76.3, 70.6, 68.8, 39.0, 30.5, 28.5; HPLC (Chiralpak AS-H, i-Propanol/Hexane=15/85, flow rate 1.0 mL/min, λ=210 nm): t$_{minor}$=14.4 min, t$_{major}$=15.9 min, ee=89%; [α]$^{25}_D$(major)=−44.5° (c=1.0 in CHCl$_3$).

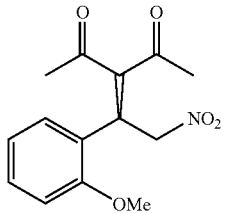

3-((R)-1-(2-methoxyphenyl)-2-nitroethyl)pentane-2,4-dione (Table 3, entry 8): The title compound was prepared according the typical procedure, as described above in 92% yield. $^1$H NMR (500 MHz, CDCl$_3$, TMS): δ=7.27 (dd, J=16.0 Hz, 1.5 Hz, 1H; Ph), 7.08 (dd, J=8.0 Hz, 1.5 Hz, 1H; Ph), 6.95-6.86 (m, 2H; Ph), 4.78 (dd, J=12.5 Hz, 8.0 Hz, 1H; CH$_2$), 4.63-4.56 (m, 2H; CH, CH$_2$), 4.52-4.46 (m, 1H; CH), 2.28 (s, 3H; CH$_3$), 1.94 (s, 3H; CH$_3$); $^{13}$C NMR (125 MHz, CDCl$_3$, TMS): δ=202.3, 201.6, 157.0, 130.2, 129.7, 123.4, 121.1, 111.2, 76.5, 68.9, 55.4, 38.9, 30.4, 28.7; HPLC (Chiralcel OD-H, i-Propanol/Hexane=15/85, flow rate 0.5 mL/min, λ=210 nm): t$_{minor}$=37.9 min, t$_{major}$=40.8 min, ee=97%; [α]$^{25}_D$(major)=−108.5° (c=2.7 in CHCl$_3$).

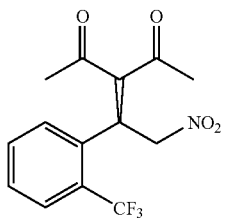

3-((R)-1-(2-(trifluoromethyl)phenyl)-2-nitroethyl)pentane-2,4-dione (Table 3, entry 9): The title compound was prepared according the typical procedure, as described above in 86% yield.

$^1$H NMR (500 MHz, CDCl$_3$, TMS): δ=7.75 (d, J=7.5 Hz, 1H; Ph), 7.53 (t, J=7.5 Hz, 1H; Ph), 7.45 (t, J=7.5 Hz, 1H; Ph), 7.27 (d, J=7.5 Hz, 1H; Ph), 4.85 (dd, J=12.0 Hz, 5.5 Hz, 1H; CH$_2$), 4.70-4.60 (m, 3H; CH, CH$_2$), 2.32 (s, 3H; CH$_3$), 2.01 (s, 3H; CH$_3$); $^{13}$C NMR (125 MHz, CDCl$_3$, TMS): δ=201.9, 200.6, 134.8, 132.6, 128.6, 127.3, 127.2, 77.6, 69.7, 37.5, 31.2, 28.3; HPLC (Chiralcel OD-H, i-Propanol/Hexane=10/90, flow rate 1.0 mL/min, λ=210 nm): t$_{minor}$=12.3 min, t$_{major}$=13.1 min, ee=93%; [α]$^{25}_D$(major)=−77.7° (c=2.8 in CHCl$_3$).

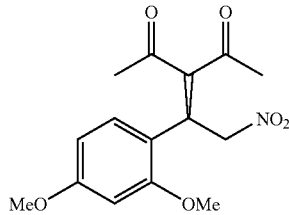

3-((R)-1-(2,4-dimethoxyphenyl)-2-nitroethyl)pentane-2,4-dione (Table 3, entry 10): The title compound was prepared according the typical procedure, as described above in 88% yield. $^1$H NMR (500 MHz, CDCl$_3$, TMS): δ=6.97 (d, J=8.5 Hz, 1H; Ph), 6.44 (d, J=2.0 Hz, 1H; Ph), 6.40 (dd, J=8.0 Hz, 2.5 Hz, 1H; Ph), 4.745 (dd, J=12.0 Hz, 8.0 Hz, 1H; CH$_2$), 4.59-4.51 (m, 2H; CH, CH$_2$), 4.43 (ddd, J=12.0 Hz, 8.0 Hz, 4.0 Hz, 1H; CH), 3.86 (s, 3H; OCH$_3$), 3.77 (s, 3H; OCH$_3$), 2.28 (s, 3H; CH$_3$), 1.93 (s, 3H; CH$_3$); $^{13}$C NMR (125 MHz, CDCl$_3$, TMS): δ=201.9, 200.6, 134.8, 132.6, 128.6, 127.3, 127.2, 77.6, 69.7, 37.5, 31.2, 28.3; HPLC (Chiralpak AS-H, i-Propanol/Hexane=15/85, flow rate 1.0 mL/min, λ=210 nm): t$_{minor}$=20.4 min, t$_{major}$=22.6 min, ee=91%; [α]$^{25}_D$(major)=−58.1° (c=0.8 in CHCl$_3$).

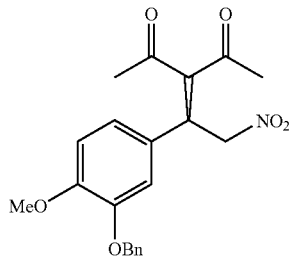

3-((R)-1-(3-(benzyloxy)-4-methoxyphenyl)-2-nitroethyl)pentane-2,4-dione (Table 3, entry 11): The title compound was prepared according the typical procedure, as described above in 78% yield. $^1$H NMR (500 MHz, CDCl$_3$, TMS): δ=7.45-7.28 (m, 5H; Ph), 6.81 (d, J=8.5 Hz, 1H; Ph), 6.71 (dd, J=8.0 Hz, 1.5 Hz, 1H; Ph), 6.66 (d, J=1.5 Hz, 1H; Ph), 5.13 (dd, J=11.5 Hz, 7.0 Hz, 2H; CH$_2$), 4.53 (d, J=6.0 Hz, 2H; OCH$_2$), 4.22 (d, J=11.0 Hz, 1H; CH), 4.12-4.06 (m, 1H; CH), 3.86 (s, 3H; CH$_3$), 2.24 (s, 3H; CH$_3$), 1.78 (s, 3H; CH$_3$); $^{13}$C NMR (125 MHz, CDCl$_3$, TMS): δ=201.8, 201.1, 149.7, 148.1, 136.7, 128.6, 128.0, 127.9, 127.4, 120.8, 114.0, 112.0, 78.3, 71.0, 70.7, 55.9, 42.3, 30.3, 29.4; HPLC (Chiralpak AS-H, i-Propanol/Hexane=15/85, flow rate 1.0 mL/min, λ=210 nm): t$_{minor}$=27.9 min, t$_{major}$=49.4 min, ee=88%; [α]$^{25}_D$(major)=−43.8° (c=1.5 in CHCl$_3$).

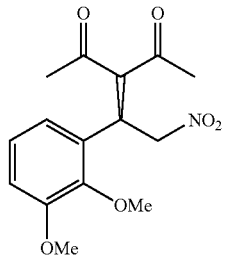

3-((R)-1-(2,3-dimethoxyphenyl)-2-nitroethyl)pentane-2,4-dione (Table 3, entry 12): The title compound was prepared according the typical procedure, as described above in 87% yield. $^1$H NMR (500 MHz, CDCl$_3$, TMS): δ=6.98 (t, J=8.0 Hz, 1H; Ph), 6.86 (d, J=8.0 Hz, 1H; Ph), 6.67 (d, J=8.0 Hz, 1H; Ph), 4.76 (dd, J=12.0 Hz, 8.0 Hz, 1H; CH$_2$), 4.76 (dd, J=12.0 Hz, 4.0 Hz, 1H; CH), 4.60-4.54 (m, 1H; CH), 4.47 (d, J=10.0 Hz, 1H; CH$_2$), 3.96 (s, 3H; CH$_3$), 3.86 (s, 3H; CH$_3$), 2.25 (s, 3H; CH$_3$), 2.04 (s, 3H; CH$_3$); $^{13}$C NMR (125 MHz, CDCl$_3$, TMS): δ=202.4, 201.4, 152.8, 146.7, 129.1, 124.3, 120.2, 112.5, 76.9, 69.5, 60.8, 55.6, 37.4, 30.9, 29.0; HPLC (Chiralpak AS-H, i-Propanol/Hexane=15/85, flow rate 1.0 mL/min, λ=210 nm): $t_{minor}$=13.6 min, $t_{major}$=16.8 min, ee=92%; $[α]^{25}_D$(major)=104.0° (c=2.8 in CHCl$_3$).

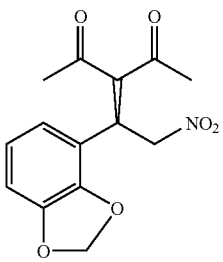

3-((R)-1-(benzo[d][1,3]dioxol-4-yl)-2-nitroethyl)pentane-2,4-dione (Table 3, entry 13): The title compound was prepared according the typical procedure, as described above in 91% yield. $^1$H NMR (500 MHz, CDCl$_3$, TMS): δ=6.74 (d, J=8.0 Hz, 1H; Ph), 6.68-6.62 (m, 2H; Ph), 5.95 (s, 2H; OCH$_2$O), 4.57 (d, J=7.0 Hz, 2H; CH, CH$_2$), 4.31 (d, J=11.0 Hz, 1H; CH$_2$), 4.20-4.14 (m, 1H; CH), 2.29 (s, 3H; CH$_3$), 1.99 (s, 3H; CH$_3$); $^{13}$C NMR (125 MHz, CDCl$_3$, TMS): δ=201.7, 200.9, 148.3, 147.6, 129.3, 121.4, 108.8, 108.1, 101.4, 78.3, 70.8, 42.5, 30.4, 29.5; HPLC (Chiralpak AD, i-Propanol/Hexane=25/75, flow rate 0.5 mL/min, λ=210 nm): $t_{minor}$=14.7 min, $t_{major}$=24.0 min, ee=80%; $[α]^{25}_D$(major)=−65.3 (c=1.0 in CHCl$_3$).

Procedure for Synthesis of α-phenyl-β-alanine 4a (Scheme 1):

Baeyer-Villiger Oxidation of 3a: To a stirred suspension of 3a (124.5 mg, 0.5 mmol), K$_2$CO$_3$ (691 mg, 5 mmol, 10 equiv), and TBAI (37 mg, 0.1 mmol, 20 mol %) in CH$_2$Cl$_2$, acetone, and water (1/1/1, 15 mL) was added a solution of Oxone® (1.5 g, 2.5 mmol, 5 equiv) in 15 mL of water over 30 min at 0° C. When being completed the addition, resulting white suspension was diluted with water and extracted with CH$_2$Cl$_2$. Organic extract was dried over Na$_2$SO$_4$ and filtrated. After being concentrated, resulting clear oil α-acetoxy-γ-nitroketone was used for next reaction without further purification.

Synthesis of α-phenyl-β-alanine 4a: To a solution of crude α-acetoxy-γ-nitroketone in 5 mL of toluene was added a 1 M solution of DIBAH in Et$_2$O (1.8 mL, 1.8 mmol) at −78° C. under N$_2$. Resulting solution was stirred for 2 h and quenched with 1 M aqueous solution of NaHSO$_4$. The mixture was extracted with CH$_2$Cl$_2$ and the organic phase was dried over MgSO$_4$. The crude residue was used for next reaction without further purification. Obtained crude diol was dissolved into 2 mL of 1,4-dioxane under N$_2$. To the solution was added H$_2$O (1 mL), Na$_2$CO$_3$ (27 mg, 0.26 mmol), NaIO$_4$ (434 mg, 2.0 mmol), and KMnO$_4$ (16 mg, 0.1 mmol) at room temperature and resulting biphasic solution was stirred for 24 h. The reaction mixture was diluted with EtOAc and 1 M aqueous solution of NaHSO$_4$. After phase-separation, the organic phase was concentrated. The residue was dissolved into MeOH (10 ml) for hydrogenation with 10% Pd/C at 50 Psi for overnight. The resulting solution was dissolved into saturated aqueous NaHCO$_3$ and extracted with Et$_2$O. The aqueous solution passed through a small pad of celite. Recrystallization from ethanol/water gave the title compound 4a as white solid in 38% yield (4 steps) ($[α]^{25}_D$=+88.20, c=0.5, H$_2$O). $^1$H NMR (500 MHz, D$_2$O, TMS): δ=7.46-7.29 (m, 5H; Ph), 3.78 (t, J=7.0 Hz, 1H; CH), 3.45 (dd, J=12.5 Hz, 8.0 Hz, 1H; CH$_2$), 3.27 (dd, J=12.5 Hz, 7.5 Hz, 1H; CH$_2$); $^{13}$C NMR (125 MHz, D$_2$O+CD$_3$OD, TMS): δ=179.1, 138.6, 130.3, 129.3, 129.0, 52.6, 43.6; The absolute stereochemistry was determined to be (R) configuration by comparison with optical rotation of literature value[4] ($[α]^{25}_D$=+850, c=0.2, H$_2$O) for the R configuration isomer.

General Procedure for Baylis-Hillman Reaction (Table 2): The catalyst amino-thiourea IV (10 mg, 0.019 mmol) was added to a vial containing 2-Cyclohexen-1-one 1a (36 μL, 0.374 mmol) in CH$_3$CN (1 mL) at 0° C. The mixture was stirred vigorously for 10 min, and then aldehyde 2 (27 μL, 0.187 mmol) was added. After 48-120 h of stirring, the reaction mixture was concentrated in vacuo. The residue was then purified by flash silica gel chromatography, eluting with EtOAc/Hexane (1:10 to 1:2) to afford a clear oil

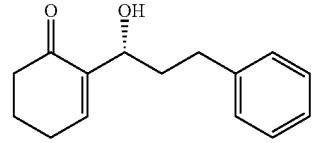

2-((R)-1-hydroxy-3-phenylpropyl)cyclohex-2-enone (Table 2, entry 1): The reaction was carried out following the general procedure to provide a clear oil (35 mg, 80%). $^1$H NMR (500 MHz, CDCl$_3$): δ 7.30-7.14 (m, 4H), 6.86 (t, 1H, J=4.0 Hz), 4.31 (dd, 1H, J=8.0 Hz, 5.0 Hz), 3.00 (bs, 1H), 2.85-2.77 (m, 1H), 2.70-2.61 (m, 1H), 2.44-2.33 (m, 4H), 2.04-1.87 (m, 4H); $^{13}$C NMR (125 MHz, CDCl$_3$): δ 200.7, 146.0, 141.8, 140.6, 128.4, 128.3, 125.8, 71.1, 38.6, 37.6, 32.2, 25.6, 22.5; $[α]^{25}_D$=−49.4 (c=0.5, CHCl$_3$); HPLC (Daicel CHIRALCEL OD-H, Hexane/2-PrOH=90:10, flow rate 1.0 ml/min, λ=254 nm); $t_R$=12.62 (minor), 9.62 (major) min.

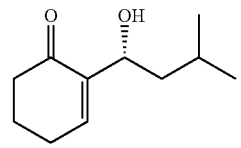

2-((R)-1-hydroxy-3-methylbutyl)cyclohex-2-enone (Table 2, entry 2): The reaction was carried out following the general procedure to provide a clear oil (25 mg, 72%). $^1$H NMR (500 MHz, CDCl$_3$): δ 6.87 (t, 1H, J=4.0 Hz), 4.38 (bs, 1H), 2.87 (d, 1H, J=6.0 Hz), 2.46-2.38 (m, 4H), 2.05-1.85 (m, 2H), 1.79-1.71 (m, 1H), 1.64-1.57 (m, 1H), 1.41-1.24 (m, 1H), 0.94 (d, 3H, J=4.5 Hz), 0.92 (d, 3H, J=4.5 Hz); $^{13}$C NMR (125 MHz, CDCl$_3$): δ 200.8, 145.6, 141.2, 70.0, 45.2, 38.8, 25.7, 24.7, 23.2, 22.6, 22.0; $[α]^{25}_D$=−25.0 (c=0.2, CHCl$_3$); HPLC (Daicel CHIRALPAK AS-H, Hexane/2-PrOH=90:10, flow rate 1.0 ml/min, λ=254 nm); $t_R$=6.92 (minor), 8.96 (major) min.

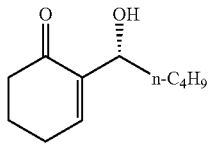

2-((R)-1-hydroxypentyl)cyclohex-2-enone (Table 2, entry 3): The reaction was carried out following the general procedure to provide a clear oil (31 mg, 84%). $^1$H NMR (500 MHz, CDCl$_3$): δ 6.87 (t, 1H, J=4.0 Hz), 4.28 (bs, 1H), 2.90 (bs, 1H), 2.50-2.38 (m, 4H), 2.05-1.95 (m, 2H), 1.70-1.56 (m, 2H), 1.45-1.22 (m, 4H), 0.91 (t, 3H, J=6.5 Hz); $^{13}$C NMR (125 MHz, CDCl$_3$): δ 200.8, 145.6, 141.2, 70.0, 45.2, 38.8, 25.7, 24.7, 23.2, 22.6, 22.0; $[α]^{25}_D$=−28.4 (c=0.4, CHCl$_3$); HPLC (Daicel CHIRALPAK AS-H, Hexane/2-PrOH=90:10, flow rate 1.0 ml/min, λ=254 nm); $t_R$=7.77 (minor), 11.25 (major) min.

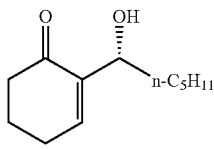

2-((R)-1-hydroxyhexyl)cyclohex-2-enone (Table 2, entry 4): The reaction was carried out following the general procedure to provide a clear oil (25 mg, 75%). $^1$H NMR (500 MHz, CDCl$_3$): δ 6.87 (t, 1H, J=4.0 Hz), 4.29 (bs, 1H), 2.90 (bs, 1H), 2.49-2.38 (m, 4H), 2.04-1.95 (m, 2H), 1.70-1.56 (m, 2H), 1.48-1.36 (m, 1H), 1.35-1.23 (m, 5H), 0.88 (t, 3H, J=6.0 Hz); $^{13}$C NMR (125 MHz, CDCl$_3$): δ 200.7, 145.8, 140.9, 71.8, 38.7, 36.2, 31.6, 25.7, 25.6, 22.6, 14.0; $[α]^{25}_D$=−44.0 (c=0.5, CHCl$_3$); HPLC (Daicel CHIRALPAK AS-H, Hexane/2-PrOH=90:10, flow rate 1.0 ml/min, λ=254 nm); $t_R$=7.42 (minor), 10.10 (major) min.

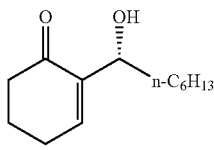

2-((R)-1-hydroxyheptyl)cyclohex-2-enone (Table 2, entry 5): The reaction was carried out following the general procedure to provide a clear oil (28 mg, 71%). $^1$H NMR (500 MHz, CDCl$_3$): δ 6.87 (t, 1H, J=4.0 Hz), 4.28 (dd, 1H, J=13.0 Hz, 6.0 Hz), 2.88 (d, 1H, 7.0 Hz), 2.48-2.38 (m, 4H), 2.04-1.95 (m, 2H), 1.70-1.56 (m, 2H), 1.45-1.36 (m, 1H), 1.35-1.23 (m, 7H), 0.88 (t, 3H, J=7.0 Hz); $^{13}$C NMR (125 MHz, CDCl$_3$): δ 200.7, 145.8, 140.9, 71.9, 38.7, 36.2, 31.8, 29.1, 26.0, 25.7, 25.6, 14.1; $[α]^{25}_D$=−33.0 (c=0.1, CHCl$_3$); HPLC (Daicel CHIRALPAK AS-H, Hexane/2-PrOH=90:10, flow rate 1.0 ml/min, λ=254 nm); $t_R$=6.71 (minor), 8.79 (major) min.

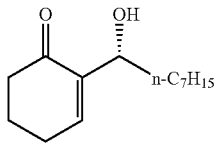

2-((R)-1-hydroxyoctyl)cyclohex-2-enone (Table 2, entry 6): The reaction was carried out following the general procedure to provide a clear oil (31 mg, 74%). $^1$H NMR (500 MHz, CDCl$_3$): δ 6.87 (t, 1H, J=4.0 Hz), 4.28 (dd, 1H, J=12.0 Hz, 6.0 Hz), 2.89 (d, 1H, 6.5 Hz), 2.47-2.38 (m, 4H), 2.04-1.95 (m, 2H), 1.70-1.56 (m, 2H), 1.45-1.36 (m, 1H), 1.35-1.23 (m, 9H), 0.88 (t, 3H, J=6.5 Hz); $^{13}$C NMR (125 MHz, CDCl$_3$): δ 200.7, 145.8, 140.9, 71.8, 38.7, 36.2, 31.8, 29.4, 29.2, 26.0, 25.7, 22.6, 22.5, 14.1; $[α]^{25}_D$=−28.2 (c=0.5, CHCl$_3$); HPLC (Daicel CHIRALPAK AS-H, Hexane/2-PrOH=90:10, flow rate 1.0 ml/min, λ=254 nm); $t_R$=6.24 (minor), 8.13 (major) min.

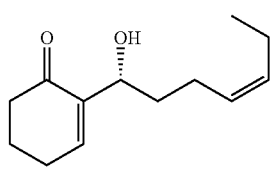

2-((R,Z)-1-hydroxyhept-4-enyl)cyclohex-2-enone (Table 2, entry 7): The reaction was carried out following the general procedure to provide a clear oil (32 mg, 82%). $^1$H NMR (500 MHz, CDCl$_3$): δ 6.87 (t, 1H, J=4.0 Hz), 5.43-5.29 (m, 2H), 4.29 (dd, 1H, J=13.0 Hz, 7.5 Hz), 2.94 (d, 1H, 7.0 Hz), 2.48-2.38 (m, 4H), 2.20-1.95 (m, 6H), 1.75-1.60 (m, 2H), 0.93 (t, 3H, J=7.0 Hz); $^{13}$C NMR (125 MHz, CDCl$_3$): δ 200.7, 146.0, 140.7, 132.4, 128.3, 71.4, 38.7, 36.1, 25.7, 23.7, 22.6, 20.5, 14.3; $[α]^{25}_D$=−26.5 (c=0.4, CHCl$_3$); HPLC (Daicel CHIRALPAK AS-H, Hexane/2-PrOH=90:10, flow rate 1.0 ml/min, λ=254 nm); $t_R$=7.72 (minor), 10.67 (major) min.

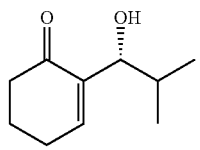

2-((R)-1-hydroxy-2-methylpropyl)cyclohex-2-enone (Table 2, entry 8): The reaction was carried out following the general procedure to provide a clear oil (20 mg, 63%). $^1$H NMR (500 MHz, CDCl$_3$): δ 6.83 (t, 1H, J=4.0 Hz), 3.87 (t, 1H, J=8.5 Hz), 2.47-2.38 (m, 4H), 2.05-1.88 (m, 3H), 0.97 (d, 3H, J=6.5 Hz), 0.80 (d, 3H, J=6.5 Hz); $^{13}$C NMR (125 MHz, CDCl$_3$): δ 201.8, 147.1, 139.6, 78.6, 38.8, 33.1, 25.7, 22.6, 19.9, 18.3; $[α]^{25}_D$=−48.0 (c=0.1, CHCl$_3$); HPLC (Daicel CHIRALPAK AS-H, Hexane/2-PrOH=90:10, flow rate 1.0 ml/min, λ=254 nm); $t_R$=90.11 (minor), 15.11 (major) min.

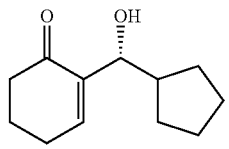

2-((R)-cyclopentyl(hydroxy)methyl)cyclohex-2-enone (Table 2, entry 9): The reaction was carried out following the general procedure to provide a clear oil (26 mg, 76%). $^1$H NMR (500 MHz, CDCl$_3$): δ 6.84 (t, 1H, J=4.0 Hz), 3.94 (t, 1H, J=7.5 Hz), 3.01 (d, 1H, J=6.0 Hz), 2.47-2.37 (m, 4H), 2.25-2.16 (m, 1H), 2.04-1.92 (m, 2H), 1.88-1.80 (m, 1H), 1.67-1.40 (m, 6H), 1.12-1.03 (m, 1H); $^{13}$C NMR (125 MHz, CDCl$_3$): δ 201.0, 146.6, 140.3, 45.0, 38.8, 30.0, 29.5, 25.7, 25.5, 22.5; $[α]^{25}_D$=−57.0 (c=0.7, CHCl$_3$); HPLC (Daicel CHIRALPAK AS-H, Hexane/2-PrOH=90:10, flow rate 1.0 ml/min, λ=254 nm); $t_R$=10.01 (minor), 15.45 (major) min.

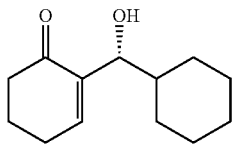

2-((R)-cyclohexyl(hydroxy)methyl)cyclohex-2-enone (Table 2, entry 10): The reaction was carried out following the general procedure to provide a clear oil (26 mg, 67%). $^1$H NMR (500 MHz, CDCl$_3$): δ 6.78 (t, 1H, J=4.5 Hz), 3.85 (d, 1H, J=8.0 Hz), 2.92 (bs, 1H), 2.48-2.37 (m, 4H), 2.05-1.92 (m, 3H), 1.79-1.53 (m, 4H), 1.45-1.37 (m, 1H), 1.25-1.05 (m, 3H), 0.97-0.80 (m, 2H); $^{13}$C NMR (125 MHz, CDCl$_3$): δ 200.9, 147.3, 139.3, 78.1, 42.6, 38.8, 30.2, 29.0, 26.4, 26.1, 25.9, 25.7, 22.6; $[α]^{25}_D$=−73.7 (c=0.3, CHCl$_3$); HPLC (Daicel CHIRALPAK AS-H, Hexane/2-PrOH=90:10, flow rate 1.0 ml/min, k=254 nm); $t_R$=10.35 (minor), 14.07 (major) min.

While the invention has been described hereinabove with reference to the detailed written description and the examples presented above, those of ordinary skill will recognize that the scope of the invention is presented in the following claims without limitation.

REFERENCES

[1] P. Perlmutter, *Conjugate Addition Reactions in Organic Synthesis*, Pergamon, Oxford, 1992.

[2] For recent reviews of asymmetric Michael addition reactions, see: a) N. Krause, A. Hoffmann-Roder, *Synthesis* 2001, 171; b) O. M. Berner, L. Tedeschi, D. Enders, *Eur. J. Org. Chem.* 2002, 1877-1894; c) J. Christoffers, A. Baro, *Angew. Chem.* 2003, 115, 1726; J. Christoffers, A. Baro, *Angew. Chem. Int. Ed,* 2003, 42, 1688; d) M. Sibi, S. Manyem, *Tetrahedron* 2001, 56, 8033.

[3] (a) N. Ono, H. Miyake, A. Kamimura, L. Hamamoto, R. Tamura, A. Kaji, *Tetrahedron* 1985, 41, 4013. (b) T. A. Johnson, D. O. Jang, B. W. Slafer, M. D. Curtis, P. Beak, *J. Am. Chem. Soc.* 2002, 11689. (c) H. Schäfer, D. Seebach, *Tetrahedron* 1995, 51, 2305. (d) A. M. Rouhi, C & En. 2004, 82, 41.

[4] (a) N. Kobayashi, K. Iwai, *J. Org. Chem.* 1981, 46, 1823. (b) C. A. Luchaco-Cullis, A. H. Hoveyda, *J. Am. Chem. Soc.* 2002, 124, 8192. (c) A. Alexakis, C. Benhaim, S. Rosset, M. Humam, *J. Am. Chem. Soc.* 2002, 124, 5262. (d) A. Rimkus, N. Sewald, *Org. Lett.* 2003, 5, 79.

[5] For organocatalytic asymmetric Michael addition of aldehydes and ketones to nitroolefins, see: a) W. Wang, J. Wang, H. Li, *Angew. Chem.* 2005, 117, 1395; *Angew. Chem. Int. Ed.* 2005, 43, 1369; b) B. List, P. Pojarliev, H. J. Martin, *Org. Lett.* 2001, 3, 2423; c) D. Ender, A. Seki, *Synlett* 2002, 26; d) N. Mase, R. Thayumanavan, F. Tanaka, C. F. Barbas, III, *Org. Lett.* 2004, 6, 2527; e) J. M. Betancort, K. Sakthivel, R. Thayumanavan, F. Tanaka, C. F. Barbas, III, *Synthesis* 2004, 1509; f) O. Andrey, A. Alexakis, G. Bernardinelli, *Org. Lett.* 2003, 5, 2559; g) T. Ishii, S. Fiujioka, Y. Sekiguchi, H. Kotsuki, *J. Am. Chem. Soc.* 2004, 126, 9558; h) A. J. A. Cobb, D. A. Longbottom, D. M. Shaw, S. V. Ley, *Chem. Commun.* 2004, 1808; i) Y. Hayashi, T. Gotoh, T. Hayasji, M. Shoji, *Angew. Chem.* 2005, 117, 4284; Y. Hayashi, T. Gotoh, T. Hayasji, M. Shoji, *Angew. Chem. Int. Ed.* 2005, 44, 4212; j) P. Kotrusz, S. Toma, H.-S. Schmalz, A. Adler, *Eur. J. Org. Chem.* 2005, 1577.

[6] For organocatalytic asymmetric Michael addition of malonates to nitroolefins, see: a) T. Okino, Y. Hoashi, Y. Takemoto, *J. Am. Chem. Soc.* 2003, 125, 12672; b) T. Okino, Y. Hoashi, T. Furukawa, X. Xu, Y. Takemoto, *J. Am. Chem. Soc.* 2005, 127, 119; c) H. Li, Y. Wang, L. Tang, L. Deng, *J. Am. Chem. Soc.* 2004, 126, 9906.

[7] For organocatalytic asymmetric Michael addition of ketoesters to nitroolefins, see: H. Li, Y. Wang, L. Tang, F. Wu, X. Liu, C. Guo, B. M. Foxman, L. Deng, *Angew. Chem. Int. Ed.* 2005, 44, 105.

[8] For reviews related to ureas/thioureas catalysis, see: a) P. M. Pihko, *Angew. Chem. Int. Ed.* 2004, 43, 2062; b) J. Seayad, B. List, *Org. Biomol. Chem.* 2005, 3, 719.

[9] For Jacobesn's ureas and thioureas for catalysts, see: a) M. S. Sigman, E. N. Jacobsen, *J. Am. Chem. Soc.* 1998, 120, 4901; b) M. S. Sigman, P. Vachal, E. N. Jacobsen, *Angew. Chem.* 2000, 112, 1336; M. S. Sigman, P. Vachal, E. N. Jacobsen, *Angew. Chem. Int. Ed.* 2000, 39, 1279; c) P. Vachal, E. N. Jacobsen, *J. Am. Chem. Soc.* 2002, 124, 10012; d) T. P. Yoon, E. N. Jacobsen, *Angew. Chem.* 2005, 117, 470; T. P. Yoon, E. N. Jacobsen, *Angew. Chem. Int. Ed.* 2005, 44, 466; e) G. D. Joly, E. N. Jacobsen, *J. Am. Chem. Soc.* 2004, 126, 4102; g) M. S. Taylor, E. N. Jacobsen, *J. Am. Chem. Soc.* 2004, 126, 10558.

[10] For Takemoyo's amine thioureas for catalysis: see: a) T. Okino, S, Nakamura, T. Furukawa, Y. Takemoto, *Org. Lett.* 2004, 6, 625; b) Y. Hoashi, T. Okino, Y. Takemoto, *Angew. Chem.* 2005, 117, 4100; Y. Hoashi, T. Okino, Y. Takemoto, *Angew. Chem. Int. Ed.* 2005, 44, 4032; and ref 6a and 6b.

[11] B. Vakulya, S. Varga, A. Csampai, T. Soos, *Org. Lett.* 2005, 7, 1967.

[12] For a review of "privileged" structures in catalysis, see: T. P. Yoon, E. N. Jacobsen, *Science* 2003, 299, 1691.

[13] For its preparation, see the supporting information.

[14] Other solvents also were tested: CHCl$_3$: 4.5 h (reaction time), 98% yield, 95% ee; ethyl vinyl ether: 7.0 h, 89% yield, 91% ee; anisole: 7.0 h, 93% yield, 91% ee; ethylene glycol dimethyl ether: 7.0 h, 90% yield, 92% ee and DMF: 4.0 h, 94% yield, 4 ee %.

[15] H. M. L. Davies, P. Ren, *Tetrahedron Lett.* 2001, 42, 3149.

(a) Set of References

Second Set (1a) (a) Basavaiah, D.; Rao, A. J.; Satyanarayana, T. *Chem. Rev.* 2003, 103, 811. (b) Langer, P. *Angew. Chem. Int. Ed.* 2000, 39, 3049.

(2a) For selected examples of the MBH reactions, see: (a) Iwabuchi, Y.; Nakatani, M.; Yokoyama, N.; Hatakeyama, S. *J. Am. Chem. Soc.* 1999, 121, 10219. (b) Yang, K.-S.; Lee, W.-D.; Pan, J.-F.; Chen. K. *J. Org. Chem.* 2003, 68, 915. (c) McDougal, N. T.; Schaus, S. E. *J. Am. Chem. Soc.* 2003, 125, 12094. (d) Shi, M.; Jiang, J.-K.; Li, C.-Q. *Tetrahedron Lett.* 2001, 42, 127. (e) Imbriglio, J. E.; Vasbinder, M. M.; Miller, S. J. *Org. Lett.* 2003, 5, 3741. (f) Oishi, T.; Oguri, H.; Hirama, M. *Tetrahedron: Asymmetry* 1995, 6, 1241. (g) Marko, I. E.; Giles, P. R.; Hindley, N. J. *Tetrahedron* 1997, 53, 1015. (h) Barrett, A. G. M.; Cook, A. S.; Kamimura, A. *Chem. Commun.* 1998, 2533. (i) Sohtome, Y.; Tanatani, A.; Hashimoto, Y.; Nagasawa, K. *Tetrahedron Lett.* 2004, 45, 5589. (j) Karur, S.; Hardin, J.; Headley, A.; Li, G. *Tetrahedron Lett.* 2003, 44, 2991. (k) Pei, W.; Wei, H.-X.; Li, G. *Chem. Commun.* 2002, 2412. (l) Pei, W.; Wei, H.-X.; Li, G. *Chem. Commun.* 2002, 1856.

(3a) aza-MBH reactions also have been studied; for selected examples, see: (a) Shi, M.; Chen, L.-H.; Li, C.-Q. *J. Am. Chem. Soc.* 2005, 127, 3790. (b) Shi, Y. *Acc. Chem. Res.*

2004, 37, 4886. (c) Shi, M.; Xu, Y.-M. *Angew. Chem. Int. Ed.* 2002, 41, 4507. (d) Perlmutter, P.; Teo, C. C. *Tetrahedron Lett.* 1984, 25, 5951. (e) Balan, D.; Adolfsson, H. *J. Org. Chem.* 2001, 66, 6498. (f) Bertenshaw, S.; Kahn, M. *Tetrahedron Lett.* 1989, 30, 2731. (g) Aggarwal, V. K.; Mereu, A.; Tarver, G. J.; McCague, R. *J. Org. Chem.* 1998, 63, 7183. (h) Azizi, N.; Saidi, M. R. Tetrahedron Lett. 2002, 43, 4305. (i) Richter, H.; Jung, G. *Tetrahedron Lett.* 1998, 39, 2729. (j) Takagi, M.; Yamamoto, K. *Tetrahedron* 1991, 47, 8869. (k) Matsui, K.; Takizawa, S.; Sasai, H. *J. Am. Chem. Soc.* 2005, 127, 3680.

(4a) (a) Shibasaki, M.; Sasai, H.; Arai, T. *Angew. Chem. Int. Ed.* 1997, 36, 1236. (b) Wang, W.; Wang, J.; Li, H. *Angew. Chem. Int. Ed.* 2005, 43, 1369. (c) Breinbauer, R.; Jacobsen, E. N. *Angew. Chem. Int. Ed.* 2000, 39, 3604.

(5a) For recent reviews related to use of ureas/thioureas as organocatalysts for organic reactions, see: (a) Seayad, J.; List, B. *Org. Biomol. Chem.* 2005, 3, 719. (b) Pihko, P. M. *Angew. Chem. Int. Ed.* 2004, 43, 2062.

(6a) For selected examples using ureas/thioureas as catalysts in asymmetric organic transformations, see: (a) Sigman, M. S.; Jacobsen, E. N. *J. Am. Chem. Soc.* 1998, 120, 4901. (b) Sigman, M. S.; Vachal, P.; Jacobsen, E. N. *Angew. Chem. Int. Ed.* 2000, 39, 1279. (c) Vachal, P.; Jacobsen, E. N. *J. Am. Chem. Soc.* 2002, 124, 10012. (d) Wenzel, A. G.; Jacobsen, E. N. *J. Am. Chem. Soc.* 2002, 124, 12964. (e) Yoon, T. P.; Jacobsen, E. N. *Angew. Chem. Int. Ed.* 2005, 44, 466. (f) Joly, G. D.; Jacobsen, E. N. *J. Am. Chem. Soc.* 2004, 126, 4102. (g) Taylor, M. S.; Jacobsen, E. N. *J. Am. Chem. Soc.* 2004, 126, 10558. (j) Okino, T.; Hoashi, Y.; Takemoto, Y. *J. Am. Chem. Soc.* 2003, 125, 12672. (i) Okino, T.; Hoashi, Y.; Furukawa, T.; Xu, X.; Takemoto, Y. *J. Am. Chem. Soc.* 2005, 127, 119. (j) Okino, T.; Nakamura, S.; Furukawa, T.; Takemoto, Y. *Org. Lett.* 2004, 6, 625. (k) Hoashi, Y.; Okino, T.; Takemoto, Y. *Angew. Chem. Int. Ed.* 2005, 44, 4032. (l) Vakulya, B.; Varga, S.; Csampai, A.; Soos, T. *Org. Lett.* 2005, 7, 1967.

(7a) For an excellent review of "privileged" structures in catalysis, see: Yoon, T. P.; Jacobsen, E. N. *Science* 2003, 299, 1691.

(8a) (a) Etter, M. C. *Acc. Chem. Res.* 1990, 23, 120. (b) Etter, M. C.; Panunto, T. W. *J. Am. Chem. Soc.* 1988, 110, 5896. (c) Etter, M. C.; Urbanczyk-Lipkowska, Z.; Zia-Ebrahimi, M.; Panunto, T. W. *J. Am. Chem. Soc.* 1990, 112, 8415.

(9a) Other solvents were also screened: THF: 67% yield, 64% ee; CHCl$_3$: 84% yield, 70% ee; xylenes: 73% yield, 74% ee; PhCF$_3$: 77% yield, 73% ee; xylenes: 73% yield, 74% ee; anisole: 65% yield, 71% ee; tBuOMe: 72% yield, 69% ee; CH$_3$CN/Et$_2$O (v/v, 1/1): 83% yield, 74% ee; tBuOME/PhCF$_3$: (v/v, 1/9): 80% yield, 63% ee; 1,4-dioxane: 61% yield, 77% ee; and DMF: 38% yield, 61% ee.

The invention claimed is:
1. A compound according to the structure:

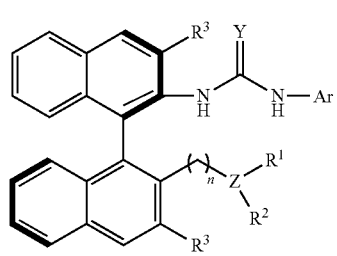

I

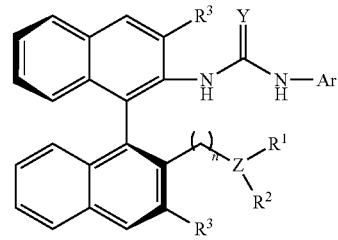

II

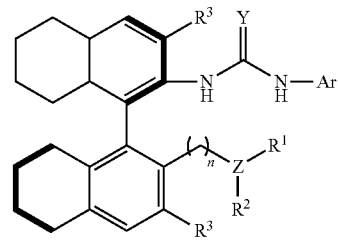

III

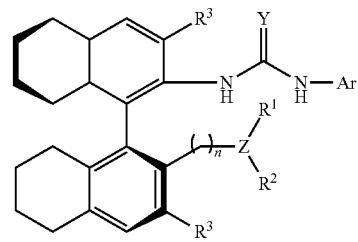

IV

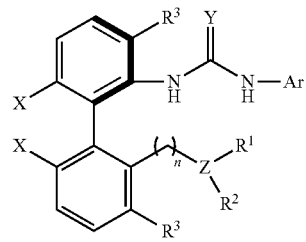

V

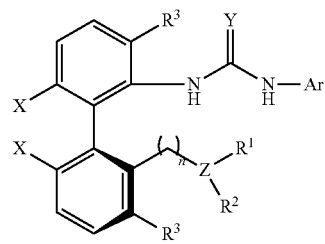

VI

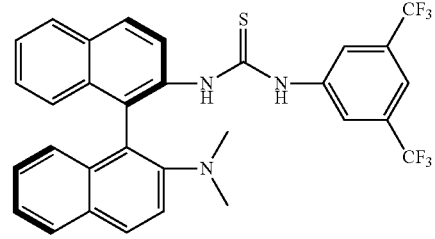

VII

Where Y is O or S;

Z is N;

n is 0-6;

$R^1$ and $R^2$ are independently H, or a $C_1$-$C_{10}$ hydrocarbyl group optionally substituted with an electron, withdrawing group or a $C_1$-$C_6$ alkyl group or a O—($C_1$-$C_6$) alkoxy group;

$R^3$ is H, halogen, CN, $NO_2$, a $CO_2R$ group, wherein R is an aromatic group which is optionally substituted with an electron withdrawing group or a $C_1$-$C_6$ alkyl group or a O—($C_1$-$C_6$) alkoxy group, or $C_1$-$C_6$ alkyl group which is optionally substituted with an electron withdrawing group or a $C_1$-$C_6$ alkyl group or a O—($C_1$-$C_6$) alkoxy group;

Ar is an aromatic group which is optionally substituted with an electron withdrawing group or a $C_1$-$C_6$ alkoxy group or O—($C_1$-$C_6$) alkoxy group;

X is an aromatic group which is optionally substituted with an electron withdrawing group or a $C_1$-$C_6$ alkyl group, $OR^4$ or $N(R^4)_2$, where each $R^4$ is independently $C_1$-$C_6$ alkyl group which is optionally substituted with an electron withdrawing group or a $C_1$-$C_6$ alkyl group, $C_3$-$C_7$ carbocyclic group which is optionally substituted with an electron withdrawing group or a $C_1$-$C_6$ alkyl group or a O—($C_1$-$C_6$) alkoxy group, or an aromatic group which is optionally substituted with an electron withdrawing group or a $C_1$-$C_6$ alkyl group or a O—($C_1$-$C_6$) alkoxy group, or a salt thereof.

2. The compound according to claim 1 wherein $R^1$ and $R^2$ are $C_1$-$C_8$ alkyl groups.

3. The compound according to claim 1 wherein $R^1$ and $R^2$ are methyl groups.

4. The compound according to claim 2 wherein Y is S, n is 0 and Z is N.

5. The compound according to claim 1 wherein Ar is a phenyl group which is optionally substituted by an electron withdrawing group.

6. The compound according to claim 5 wherein said electron withdrawing group is selected from the group consisting of $CF_3$, $CF_2CF_3$, F, Cl, Br, I, CN and $NO_2$.

7. The compound according to claim 6 wherein said electron withdrawing group is $NO_2$ or $CF_3$.

8. The compound according to claim 1 wherein $R^3$ is $CF_3$, F, CN or $NO_2$.

9. The compound according to claim 1 wherein R is an optionally substituted phenyl group.

10. The compound according to claim 1 wherein X is an optionally substituted phenyl group.

11. The compound according to claim 10 wherein said phenyl group is substituted with an electron withdrawing group selected from the group consisting of $CF_3$, $CF_2CF_3$, F, Cl, Br, I, CN and $NO_2$.

12. The compound according to claim 1 having the chemical structure I where Y is S, n is 0 or 1 and Z is N.

13. The compound according to claim 1 having the chemical structure II where Y is S, n is 0 or 1 and Z is N.

14. The compound according to claim 1 having chemical structure III where Y is S, n is 0 or 1 and Z is N.

15. The compound according to claim 1 having chemical structure IV where Y is S, n is 0 or 1 and Z is N.

16. The compound according to claim 1 having chemical structure V where Y is S, n is 0or 1 and Z is N.

17. The compound according to claim 1 having chemical structure VI where Y is S, n is 0or 1 and Z is N.

18. The compound according to claim 1 having chemical structure VU.

19. The compound according to claim 1 wherein said electron withdrawing group is selected from the group consisting of $CF_3$, $CF_2CF_3$, F, Cl, Br, I, CN and $NO_2$.

* * * * *